(12) United States Patent
Merlo et al.

(10) Patent No.: US 10,793,612 B2
(45) Date of Patent: Oct. 6, 2020

(54) PROCESS FOR DESIGNING DIVERGED, CODON-OPTIMIZED LARGE REPEATED DNA SEQUENCES

(71) Applicant: Dow AgroSciences LLC, Indianapolis, IN (US)

(72) Inventors: Donald J. Merlo, Carmel, IN (US); Ignacio Larrinua, Indianapolis, IN (US); Scott Bevan, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 964 days.

(21) Appl. No.: 14/415,115

(22) PCT Filed: Jul. 16, 2013

(86) PCT No.: PCT/US2013/050744
§ 371 (c)(1),
(2) Date: Jan. 15, 2015

(87) PCT Pub. No.: WO2014/014950
PCT Pub. Date: Jan. 23, 2014

(65) Prior Publication Data
US 2015/0175672 A1 Jun. 25, 2015

Related U.S. Application Data

(60) Provisional application No. 61/672,114, filed on Jul. 16, 2012.

(51) Int. Cl.
C07K 14/415 (2006.01)
C12N 15/63 (2006.01)
C12N 15/82 (2006.01)

(52) U.S. Cl.
CPC ............ *C07K 14/415* (2013.01); *C12N 15/63* (2013.01); *C12N 15/8216* (2013.01)

(58) Field of Classification Search
None
See application file for complete search history.

(56) References Cited

U.S. PATENT DOCUMENTS

| 5,830,713 A | 11/1998 | Ferrari et al. |
| 6,355,776 B1 | 3/2002 | Ferrari et al. |
| 7,368,629 B2 | 5/2008 | Verbsky |
| 2004/0152108 A1 | 8/2004 | Keith et al. |
| 2007/0292918 A1 | 12/2007 | Stelman et al. |
| 2009/0093621 A1 | 4/2009 | Ferrari et al. |
| 2012/0142611 A1 | 6/2012 | Stumpp et al. |

FOREIGN PATENT DOCUMENTS

| WO | 8803533 | 5/1988 |
| WO | 9810063 | 3/1998 |
| WO | WO201146524 A1 | 4/2011 |
| WO | 2014014950 | 1/2014 |

OTHER PUBLICATIONS

Alba et al.; Comparative Analysis of Amino Acid Repeats in Rodents and Humans; Genome Research; 14: 549-554 2004.
Gustafsson et al.; Codon bias and heterologous protein expression; Trens in Biotechnology vol. 22 No. 7 Jul. 2004; 346-353.
Katti et al.; Amino acid repeat patterns in protein sequences: Their diversity and structural-functional implications; Protein Science (2000), 9:1203-1209.
Angov, Evelina, Codon usage: nature's roadmap to expression and folding of proteins, Biotechnology Journal, 10 pages, May 12, 2011, vol. 6, No. 6.
Chung, Bevan Kai-Sheng, et al., "Computational codon optimization of synthetic gene for protein expression," BMC Systems Biology, Biomed Central Ltd, Oct. 20, 2012, p. 134, vol. 6, No. 1.
Kudla, G., et al., "Coding-sequence determinants of gene expression in *Escherichia coli*," Science Apr. 10, 2009, pp. 255-258, vol. 324, No. 5924.
Ma et al, "Phylogenetic Analysis of the pPT23A Plasmid Family of Pseudomonas syringae" Appl Environ Microbiol. Feb. 2007; 73(4): 1287-1295.
Kudla G, "Coding-Sequence Determinants of Gene Expression in *Escherichia coli*", Science, vol. 324, Nr: 5924, pp. 255-258.

*Primary Examiner* — Joseph Woitach

(57) ABSTRACT

This disclosure concerns methods for the design of synthetic nucleic acid sequences that encode polypeptide amino acid repeat regions. This disclosure also concerns the use of such sequences to express a polypeptide of interest that comprises amino acid repeat regions, and organisms comprising such sequences.

11 Claims, 10 Drawing Sheets

Specification includes a Sequence Listing.

FIG. 2.

| | | |
|---|---|---|
| Pro-Ala Rpt 1 | (SEQ ID NO:1) (1) | APAPVKAAAPAAPVASAPAPA |
| Pro-Ala Rpt 2 | (SEQ ID NO:2) (1) | APAPAAAAPAPAKAAPAAAAPA |
| Pro-Ala Rpt 3 | (SEQ ID NO:3) (1) | APAPAAAAPGPAAAAPAAAAPA |
| Pro-Ala Rpt 4 | (SEQ ID NO:4) (1) | APAPAAAAPAPAAAAPAPAPAPA |
| Pro-Ala Rpt 5 | (SEQ ID NO:5) (1) | APAPAAAAPAPAAAAPAPAAPAPAPAPA |
| Pro-Ala Rpt 6 | (SEQ ID NO:4) (1) | APAPAAAAPAPAAAAPAPAAPAPA |
| Pro-Ala Rpt 7 | (SEQ ID NO:6) (1) | APAPAAAAPAPAAAAPA |
| Pro-Ala Rpt 8 | (SEQ ID NO:4) (1) | APAPAAAAPAPAAAAPAPAAAAPA |
| Pro-Ala Rpt 9 | (SEQ ID NO:6) (1) | APAPAAAAPAPAAAAPA |
| Pro-Ala Rpt 10 | (SEQ ID NO:7) (1) | APAPAAAAPASAGAAPA |

FIG. 3.

```
Repeat 1 (SEQ ID NO:8)   (1) VSNELLEKAETVVMEVLAAKTGYETDMIEADMELE
Repeat 2 (SEQ ID NO:9)   (1) VSNELLEKAETVVMEVLAAKTGYETDMIESDMELE
Repeat 7 (SEQ ID NO:10)  (1) VSNELLEKAETVVMEVLAAKTGYETDMIESDMELE
Repeat 4 (SEQ ID NO:11)  (1) VSSELLEKAETVVMEVLAAKTGYETDMIESDMELE
Repeat 8 (SEQ ID NO:11)  (1) VSSELLEKAETVVMEVLAAKTGYETDMIESDMELE
Repeat 5 (SEQ ID NO:12)  (1) VSSELLEKAETVVMEVLAAKTGYETDMIESDMELE
Repeat 3 (SEQ ID NO:13)  (1) VSNELLEKAETVVMEVLAAKTGYETDMIESDMELE
Repeat 6 (SEQ ID NO:13)  (1) VSNELLEKAETVVMEVLAAKTGYETDMIESDMELE
Repeat 9 (SEQ ID NO:13)  (1) VSNELLEKAETVVMEVLAAKTGYETDMIESDMELE
# codons                     466266222444124644244242421326212 62

(36) TELGIDSIKRVEILSEVQAMLNVEAKDVDALSRTRTVGEVVNAMKAEIAGSS
(36) TELGIDSIKRVEILSEVQAMLNVEAKDVDALSRTRTVGEVVNAMKAEIAGSS
(36) TELGIDSIKRVEILSEVQAMLNVEAKDVDALSRTRTVGEVVNAMKAEIAGSS
(36) TELGIDSIKRVEILSEVQAMLNVEAKDVDALSRTRTVGEVVDAMKAEIAGSS
(36) TELGIDSIKRVEILSEVQAMLNVEAKDVDALSRTRTVGEVVDAMKAEIAGSS
(36) TELGIDSIKRVEILSEVQAMLNVEAKDVDALSRTRTVGEVVDAMKAEIAGSS
(36) TELGIDSIKRVEILSEVQAMLNVEAKDVDALSRTRTVGEVVDAMKAEIAGSS
(36) TELGIDSIKRVEILSEVQAMLNVEAKDVDALSRTRTVGEVVDAMKAEIAGSS
(36) TELGIDSIKRVEILSEVQAMLNVEAKDVDALSRTRTVGEVVDAMKAEIAGSS
     426432632642366242416242422466464442424124234 66
```

FIG. 4

```
Repeat 1 (SEQ ID NO:14)   (1) CGTCATGGAGCTCGAGAACCGTCATGGAGCTCCTCGCCGCCAAGACCGGCTACGAGAACCGGCTCATTGACTCCATCAAGCCGTGACTCCGAGATCCTCTC
Repeat 2 (SEQ ID NO:15)   (1) GTCTCGAACGAGCTTCTCGAGAAGGCCGAGACCGT
Repeat 3 (SEQ ID NO:16)   (1) GTCTCGAACGAGCTTCTCGAGAAGGCCGAGACCGT
Repeat 4 (SEQ ID NO:17)   (1) GTCTCGAACGAGCTTCTCGAGAAGGCCGAGACTGT
Repeat 9 (SEQ ID NO:18)   (1) GTCTCGAACGAGCTTCTCGAGAAGGCCGAGACCGT
Repeat 5 (SEQ ID NO:19)   (1) GTCTCGAGCGAGCTTCTCGAGAAGGCCGAGACTGT
Repeat 7 (SEQ ID NO:20)   (1) GTCTCGAACGAGCTTCTCGAGAAAGCCGAGACTGT
Repeat 6 (SEQ ID NO:21)   (1) GTCTCGAACGAGCTTCTCGAGAAAGCCGAGACTGT
Repeat 8 (SEQ ID NO:22)   (1) GTCTCGAGCGAGCTTCTCGAGAAGGCCGAGACCGT

(36) CGTCATGGAGGTCCTCGCCGCCAAGACCGGCTACGAGAACCGACATGATCGAGGTCGA
                         (36) CGTCATGGAGGTCCTCGCCGCCAAGACTGGCTACGAGACTGACATGATCGAGTCCGA
                         (36) CGTCATGGAGGTCCTCGCCGCCAAGACTGGCTACGAGACTGACATGATCGAGTCCGA
                         (36) CGTCATGGAGGTCCTCGCCGCCAAGACTGGCTACGAGACTGACATGATCGAGTCCGA
                         (36) CGTCATGGAGGTCCTCGCCGCCAAGACTGGCTACGAGACTGACATGATTGAGTCCGA
                         (36) CGTCATGGAGGTCCTCGCCGCCAAGACTGGCTACGAGACTGACATGATCGAGTCCGA
                         (36) CGTCATGGAGGTCCTCGCCGCCAAGACTGGCTACGAGACTGACATGATCGAGTCCGA
                         (36) CGTCATGGAGGTCCTCGCCGCCAAGACTGGCTACGAGACTGACATGATCGAGTCCGA
                         (36) CGTCATGGAGGTCCTCGCCGCCAAGACTGGCTACGAGACTGACATGATTGAGTCCGA

(93) CATGGAGCTCGAGACCGAGCTCGGCATTGACTCCATCAAGCGTGACTCCGAGATCCTCTC
                         (93) CATGGAGCTCGAGACCGAGCTCGGCATTGACTCCATCAAGCGTGTCGAGATCCTCTC
                         (93) CATGGAGCTCGAGACCGAGCTCGGCATTGACTCCATCAAGCGTGTCGAGATCCTCTC
                         (93) CATGGAGCTCGAGACCGAGCTCGGCATTGACTCCATCAAGCGTGTCGAGATTCTCTC
                         (93) CATGGAGCTCGAGACCGAGCTCGGCATTGACTCCATCAAGCGTGTCGAGATTCTCTC
                         (93) CATGGAGCTCGAGACCGAGCTCGGCATTGACTCCATCAAGCGTGTCGAGATTCTCTC
                         (93) CATGGAGCTCGAGACCGAGCTCGGCATTGACTCCATCAAGCGTGTCGAGATTCTCTC
                         (93) CATGGAGCTCGAGACTGAGCTCGGCATTGACTCCATCAAGCGTGTCGAGATCCTCTC
                         (93) CATGGAGCTCGAGACTGAGCTCGGCATTGACTCCATCAAGCGTGTCGAGATCCTCTC (150) CGAGGTCCAGGCCATGCTCAATGTCGAGGCCAAGGATGTCGATGCCCTCAGCCGCAC
                        (150) CGAGGTTCAGGCCATGCTCAACGTCGAGGCCAAGGACGTCGACGCTCTCAGCCGCAC
                        (150) CGAGGTCCAGGCCATGCTCAACGTCGAGGCCAAGGACGTCGACGCTCTCAGCCGCAC
                        (150) CGAGGTCCAGGCCATGCTCAACGTCGAGGCCAAGGACGTCGACGCTCTCAGCCGCAC
```

FIG. 4 (CONT)

```
(150)  CGAGGTTCAGGCCATGCTCAAGGTCGAGGCCAAGGACGTCGAGGCTCTCAGCCGCAC
(150)  CGAGGTTCAGGCCATGCTCAAGGTCGAGGCCAAGGACGTCGAGCGCTCTCAGCCGCAC
(150)  CGAGGTTCAGGCCATGCTCAAGGTCGAGGCCAAGGACGTCGATGCTCTCAGCCGCAC
(150)  CGAGGTTCAGGCCATGCTCAAGGTCGAGGCCAAGGACGTCGATGCCCTCAGCCGCAC
(150)  CGAGGTTCAGGCCATGCTCAAGCTCGAGGCCAAGGACGTCGATGCCCTCAGCCGCAC (207)  TCGCACTGTTGGTGAGGTTGTCAAGCCATGAAGGCCGAGATCGCTGGCAGCTCT
(207)  TCGCACTGTTGGTGAGGTCGTCAACGCCATGAAGGCCGAGATCGCTGGTGGCTCT
(207)  CCGCACTGTTGGCGAGGTCGTCGATGCCATGAAGGCCGAGATCGCTGGTGGCTCT
(207)  CCGCACTGTTGGCGAGGTCGTCGATGCCATGAAGGCCGAGATCGCTGGTGGCTCT
(207)  TCGCACTGTTGGCGAGGTCGTCGATGCCATGAAGGCCGAGATCGCTGGTGGCTCT
(207)  TCGCACTGTTGGTGAGGTCGTCGATGCCATGAAGGCCGAGATCGCTGGTGGCTCT
(207)  TCGCACTGTTGGCGAGGTCGTCGATGCCATGAAGGCCGAGATCGCTGGCAGCTCC
(207)  CCGCACTGTTGGCGAGGTTGTCGAGGTTGTCGATGCCATGAAGGCCGAGATCGCCGGCAGCTCC
(207)  CCGCACTGTTGGCGAGGTTGTCGATGCCATGAAGGCCGAGATCGCTGGTGGCTCT
```

|  | rpt1 nap9 | rpt2 nap10 | rpt3 nap10 | rpt4 nap1 | rpt5 nap10 | rpt6 nap6 | rpt7 nap9 | rpt8 nap4 | rpt9 nap10 |
|---|---|---|---|---|---|---|---|---|---|
| rpt1 nap9 | 100 | | | | | | | | |
| rpt2 nap10 | 77 | 100 | | | | | | | |
| rpt3 nap10 | 74 | 81 | 100 | | | | | | |
| rpt4 nap1 | 77 | 76 | 79 | 100 | | | | | |
| rpt5 nap10 | 74 | 74 | 80 | 80 | 100 | | | | |
| rpt6 nap6 | 77 | 77 | 74 | 77 | 78 | 100 | | | |
| rpt7 nap9 | 81 | 79 | 74 | 75 | 77 | 78 | 100 | | |
| rpt8 nap4 | 76 | 76 | 76 | 76 | 77 | 76 | 75 | 100 | |
| rpt9 nap10 | 76 | 77 | 78 | 76 | 77 | 77 | 74 | 76 | 100 |

FIG. 8

```
Repeat 1 (SEQ ID NO:35)  (1) TGTGATGGAGGTTCTCCGTGCCAAGAGACTGAGTTGCTGAGTTCTCCAACGAGTTGCTTGAGAAAGCTGAGACAGT
Repeat 3 (SEQ ID NO:36)  (1) CGTGATGGAGGTCTTGGCACTGAGACAGACCGGCTGCTCAGAGACTGGAGTCTCAAACGAACTCTTGGAGAAAGCTGAGACCGT
Repeat 4 (SEQ ID NO:37)  (1) TGTGATGGAGGTTTTGCCTGCGAAAACCAGCTGCTGCACTGAAAGACTGGAGTTTCTTCAGAACTCTTCCTGGAGAAGGCTGAGACAGT
Repeat 8 (SEQ ID NO:38)  (1) TGTGATGGAAGTCCCTTGCTGCGCATGAGACCAGCTGGTCGCTGAAACACTGGAGTCTCCTCAGAACTCCTGGAAAAGGCGAGACAGT
Repeat 5 (SEQ ID NO:39)  (1) TGTGATGGAGGTCTTTTGGCTTTGCGCACTGGAGACAACCGGCTGGTTCGCTGGAAACACTGGAGCTTTCATCGAACTCCTGGAAAAGCTGAAAATGT
Repeat 9 (SEQ ID NO:40)  (1) TGTGATGGAGGTCTTTGCTGCTTCGCACTGGAGAGACAACCGGCTGGTTCGCTGGAAACACTGGAGTCAGCAGCAATGAGCTGCTGAAAAGCTGAAAATGT
Repeat 2 (SEQ ID NO:41)  (1) TGTGATGGAGAACTCCCTTGCTGCTTGCGCACTGGAGACAACCCGGCTGGTTCACTGAAAACTGGAGTTTCTAATGAGCTGCTGAAAAGGCAGAAACTGT
Repeat 6 (SEQ ID NO:42)  (1) TGTGATGGAAGTGAAGCTCCTTGCTGGCTTGCGAAACAACTGGTTCACTGAAAACTGGAGTCAGCAATGAGTTGCTGGAGAACAGCGAAAACAGT
Repeat 7 (SEQ ID NO:43)  (1) TGTCATGGAAGTCCAAGCCATTGCAGCAATTGCGCACTGGAGACAACTGGTTACGAAAACTGGAGTCAGCAATGAGCTGCTGAGAGGCTGAAACAGT

(36) CATGGAGCTTGAGACTGAGTTGGGAATTGACAGACTCAAGAGGGTTGAATTCTTCGAGGCGGA
                         (36) CATGGAATTGCAGACAGAGTTGGGATAGAGCATGATTGACACAGCAGCATCATCAAGCCATGTGTTGAAATCCCTCAGGAGGCGGA
                         (36) TATGGAACTTGGAGACAGAGCTTGGGATCGATTGACTCCGCCATCATGATGATTGAGAGATGGTGTGAAAAGAGCCTGAGGAGGCGGA
                         (36) CATGGAACTTGGAGACCGAGCCGAGTTGGAATTGAATGACTCCATAGCCATCATCATGATTGAAAACCGTGTTGAAATCCCTCTCGAGGCGGA
                         (36) CATGGAGCTTGAAACCGAGCTTGGAATTGAATAGACAGAGCATTGCCATCATGATTGAGAACCGTGTTGTGAAATCTTGTCGAGGCGGA
                         (36) CATGGAGCTTGAAACAGAGCTTGGATTGGAATTAGAGCTTGATTCCATCATCATGATTGACCCAAGCGTGTGTGGAAATCCCTCAGGAGGCGGA
                         (36) CATGGAGCTTGAAACAGAGCTTGGATTGGAATTGATTCCATTGATTCCATCATCAAGGAGTGTTGGGAATCCCTCAGGAGGCGGA
                         (36) CATGGAATTGGGAACCGAACTTGGAATTGAATAGATTCCATCATCACGAAGAAGATCAGAGAATCGAGGTTGAGATCCTCAGGAGGCGGA
                         (36) CATGGAACTTGAGAGACGAGCTTGGGCATTGGAATAGATTCATTGACAGCAGCATCATCAAGCTGTGTGAGATCCTCAGGAGGCGGA

(93) TGAAGTCCAAGCTATGCTTAACGTTGAGGCGAAAGATGTTGATGCTCTCTCTAGGAC
                         (93) TGAGGTCCAAGCTATGCTGAACTGCTGGAACGTGGAAGCGAAGTGTTGATGCTCTTGTCCAGAAC
                         (93) TGAAGTCCAAGCCATTGCTTCAATGTTGAAGCTAAGCTAAGGATGTTGATGGAGTTCAACTTTCAAGAAC
```

FIG. 8 (CONT)

SEQUENCE LISTING

<160> NUMBER OF SEQ ID NOS: 51

<210> SEQ ID NO 1
<211> LENGTH: 21
<212> TYPE: PRT
<213> ORGANISM: Schizochytrium spp

<400> SEQUENCE: 1

Ala Pro Ala Pro Val Lys Ala Ala Ala Pro Ala Ala Pro Val Ala Ser
1               5                   10                  15

Ala Pro Ala Pro Ala
            20

<210> SEQ ID NO 2
<211> LENGTH: 22
<212> TYPE: PRT
<213> ORGANISM: Schizochytrium spp

<400> SEQUENCE: 2

Ala Pro Ala Pro Ala Ala Ala Ala Pro Ala Pro Ala Lys Ala Ala Pro
1               5                   10                  15

Ala Ala Ala Ala Pro Ala
            20

<210> SEQ ID NO 3
<211> LENGTH: 24
<212> TYPE: PRT
<213> ORGANISM: Schizochytrium spp

<400> SEQUENCE: 3

Ala Pro Ala Pro Ala Ala Ala Ala Pro Gly Pro Ala Ala Ala Ala Pro
1               5                   10                  15

Ala Pro Ala Ala Ala Ala Pro Ala
            20

<210> SEQ ID NO 4
<211> LENGTH: 24
<212> TYPE: PRT
<213> ORGANISM: Schizochytrium spp

<400> SEQUENCE: 4

Ala Pro Ala Pro Ala Ala Ala Ala Pro Ala Pro Ala Ala Ala Ala Pro
1               5                   10                  15

Ala Pro Ala Ala Pro Ala Pro Ala
            20

<210> SEQ ID NO 5
<211> LENGTH: 29
<212> TYPE: PRT
<213> ORGANISM: Schizochytrium spp

<400> SEQUENCE: 5

Ala Pro Ala Pro Ala Ala Ala Ala Pro Ala Pro Ala Ala Ala Ala Pro
1               5                   10                  15

Ala Pro Ala Ala Pro Ala Pro Ala Ala Pro Ala Pro Ala
            20                  25

<210> SEQ ID NO 6
<211> LENGTH: 24
<212> TYPE: PRT
<213> ORGANISM: Schizochytrium spp

<400> SEQUENCE: 6

Ala Pro Ala Pro Ala Ala Ala Ala Pro Ala Pro Ala Ala Ala Ala Pro
1               5                   10                  15

Ala Pro Ala Ala Pro Ala Pro Ala
            20

<210> SEQ ID NO 7
<211> LENGTH: 17
<212> TYPE: PRT
<213> ORGANISM: Schizochytrium spp

<400> SEQUENCE: 7

Ala Pro Ala Pro Ala Ala Ala Ala Pro Ala Pro Ala Ala Ala Ala Pro
1               5                   10                  15

Ala

<210> SEQ ID NO 8
<211> LENGTH: 24
<212> TYPE: PRT
<213> ORGANISM: Schizochytrium spp -continued

```
<400> SEQUENCE: 8

Ala Pro Ala Pro Ala Ala Ala Pro Ala Pro Ala Ala Ala Ala Pro
1               5                   10                  15

Ala Pro Ala Ala Ala Ala Pro Ala
            20

<210> SEQ ID NO 9
<211> LENGTH: 17
<212> TYPE: PRT
<213> ORGANISM: Schizochytrium spp

<400> SEQUENCE: 9

Ala Pro Ala Pro Ala Ala Ala Ala Pro Ala Pro Ala Ala Ala Ala Pro
1               5                   10                  15

Ala

<210> SEQ ID NO 10
<211> LENGTH: 17
<212> TYPE: PRT
<213> ORGANISM: Schizochytrium spp

<400> SEQUENCE: 10

Ala Pro Ala Pro Ala Ala Ala Ala Pro Ala Ser Ala Gly Ala Ala Pro
1               5                   10                  15

Ala

<210> SEQ ID NO 11
<211> LENGTH: 87
<212> TYPE: PRT
<213> ORGANISM: Schizochytrium spp

<400> SEQUENCE: 11

Val Ser Asn Glu Leu Leu Glu Lys Ala Glu Thr Val Val Met Glu Val
1               5                   10                  15

Leu Ala Ala Lys Thr Gly Tyr Glu Thr Asp Met Ile Glu Ala Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Met Leu Asn Val Glu Ala Lys Asp Val Asp
    50                  55                  60

Ala Leu Ser Arg Thr Arg Thr Val Gly Glu Val Val Asn Ala Met Lys
65                  70                  75                  80

Ala Glu Ile Ala Gly Ser Ser
                85

<210> SEQ ID NO 12
<211> LENGTH: 87
<212> TYPE: PRT
<213> ORGANISM: Schizochytrium spp

<400> SEQUENCE: 12

Val Ser Asn Glu Leu Leu Glu Lys Ala Glu Thr Val Val Met Glu Val
1               5                   10                  15

Leu Ala Ala Lys Thr Gly Tyr Glu Thr Asp Met Ile Glu Ser Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Met Leu Asn Val Glu Ala Lys Asp Val Asp
    50                  55                  60
```

Ala Leu Ser Arg Thr Arg Thr Val Gly Glu Val Val Asn Ala Met Lys
 65                  70                  75                  80

Ala Glu Ile Ala Gly Gly Ser
                85

<210> SEQ ID NO 13
<211> LENGTH: 87
<212> TYPE: PRT
<213> ORGANISM: Schizochytrium spp

<400> SEQUENCE: 13

Val Ser Asn Glu Leu Leu Glu Lys Ala Glu Thr Val Val Met Glu Val
 1               5                  10                  15

Leu Ala Ala Lys Thr Gly Tyr Glu Thr Asp Met Ile Glu Ser Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Met Leu Asn Val Glu Ala Lys Asp Val Asp
    50                  55                  60

Ala Leu Ser Arg Thr Arg Thr Val Gly Glu Val Val Asp Ala Met Lys
 65                  70                  75                  80

Ala Glu Ile Ala Gly Gly Ser
                85

<210> SEQ ID NO 14
<211> LENGTH: 87
<212> TYPE: PRT
<213> ORGANISM: Schizochytrium spp

<400> SEQUENCE: 14

Val Ser Ser Glu Leu Leu Glu Lys Ala Glu Thr Val Val Met Glu Val
 1               5                  10                  15

Leu Ala Ala Lys Thr Gly Tyr Glu Thr Asp Met Ile Glu Ser Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Met Leu Asn Val Glu Ala Lys Asp Val Asp
    50                  55                  60

Ala Leu Ser Arg Thr Arg Thr Val Gly Glu Val Val Asp Ala Met Lys
 65                  70                  75                  80

Ala Glu Ile Ala Gly Gly Ser
                85

<210> SEQ ID NO 15
<211> LENGTH: 87
<212> TYPE: PRT
<213> ORGANISM: Schizochytrium spp

<400> SEQUENCE: 15

Val Ser Ser Glu Leu Leu Glu Lys Ala Glu Thr Val Val Met Glu Val
 1               5                  10                  15

Leu Ala Ala Lys Thr Gly Tyr Glu Thr Asp Met Ile Glu Ser Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Met Leu Asn Val Glu Ala Lys Asp Val Asp
    50                  55                  60

```
Ala Leu Ser Arg Thr Arg Thr Val Gly Glu Val Val Asp Ala Met Lys
 65                  70                  75                  80

Ala Glu Ile Ala Gly Ser Ser
                 85
```

<210> SEQ ID NO 16
<211> LENGTH: 87
<212> TYPE: PRT
<213> ORGANISM: Schizochytrium spp

<400> SEQUENCE: 16

```
Val Ser Asn Glu Leu Leu Glu Lys Ala Glu Thr Val Val Met Glu Val
 1               5                  10                  15

Leu Ala Ala Lys Thr Gly Tyr Glu Thr Asp Met Ile Glu Ser Asp Met
                20                  25                  30

Glu Leu Glu Thr Glu Leu Gly Ile Asp Ser Ile Lys Arg Val Glu Ile
             35                  40                  45

Leu Ser Glu Val Gln Ala Met Leu Asn Val Glu Ala Lys Asp Val Asp
         50                  55                  60

Ala Leu Ser Arg Thr Arg Thr Val Gly Glu Val Val Asp Ala Met Lys
 65                  70                  75                  80

Ala Glu Ile Ala Gly Gly Ser
                 85
```

<210> SEQ ID NO 17
<211> LENGTH: 87
<212> TYPE: PRT
<213> ORGANISM: Schizochytrium spp

<400> SEQUENCE: 17

```
Val Ser Asn Glu Leu Leu Glu Lys Ala Glu Thr Val Val Met Glu Val
 1               5                  10                  15

Leu Ala Ala Lys Thr Gly Tyr Glu Thr Asp Met Ile Glu Ser Asp Met
                20                  25                  30

Glu Leu Glu Thr Glu Leu Gly Ile Asp Ser Ile Lys Arg Val Glu Ile
             35                  40                  45

Leu Ser Glu Val Gln Ala Met Leu Asn Val Glu Ala Lys Asp Val Asp
         50                  55                  60

Ala Leu Ser Arg Thr Arg Thr Val Gly Glu Val Val Asp Ala Met Lys
 65                  70                  75                  80

Ala Glu Ile Ala Gly Ser Ser
                 85
```

<210> SEQ ID NO 18
<211> LENGTH: 87
<212> TYPE: PRT
<213> ORGANISM: Schizochytrium spp

<400> SEQUENCE: 18

```
Val Ser Ser Glu Leu Leu Glu Lys Ala Glu Thr Val Val Met Glu Val
 1               5                  10                  15

Leu Ala Ala Lys Thr Gly Tyr Glu Thr Asp Met Ile Glu Ser Asp Met
                20                  25                  30

Glu Leu Glu Thr Glu Leu Gly Ile Asp Ser Ile Lys Arg Val Glu Ile
             35                  40                  45

Leu Ser Glu Val Gln Ala Met Leu Asn Val Glu Ala Lys Asp Val Asp
         50                  55                  60

Ala Leu Ser Arg Thr Arg Thr Val Gly Glu Val Val Asp Ala Met Lys
```

Ala Glu Ile Ala Gly Gly Ser
            85

<210> SEQ ID NO 19
<211> LENGTH: 87
<212> TYPE: PRT
<213> ORGANISM: Schizochytrium spp

<400> SEQUENCE: 19

Val Ser Asn Glu Leu Leu Glu Lys Ala Glu Thr Val Val Met Glu Val
1               5                   10                  15

Leu Ala Ala Lys Thr Gly Tyr Glu Thr Asp Met Ile Glu Ser Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Met Leu Asn Val Glu Ala Lys Asp Val Asp
    50                  55                  60

Ala Leu Ser Arg Thr Arg Thr Val Gly Glu Val Val Asp Ala Met Lys
65                  70                  75                  80

Ala Glu Ile Ala Gly Gly Ser
            85

<210> SEQ ID NO 20
<211> LENGTH: 261
<212> TYPE: DNA
<213> ORGANISM: Schizochytrium spp

<400> SEQUENCE: 20
gtctcgaacg agcttcttga aaggccgag actgtcgtca tggaggtcct cgccgccaag      60
accggctacg agaccgacat gatcgaggct gacatggagc tcgagaccga gctcggcatt    120
gactccatca gcgtgtcga gatcctctcc gaggtccagg ccatgctcaa tgtcgaggcc    180
aaggatgtcg atgccctcag ccgcactcgc actgttggtg aggttgtcaa cgccatgaag    240
gccgagatcg ctggcagctc t                                              261

<210> SEQ ID NO 21
<211> LENGTH: 261
<212> TYPE: DNA
<213> ORGANISM: Schizochytrium spp

<400> SEQUENCE: 21
gtctcgaacg agcttctcga aaggccgag accgtcgtca tggaggtcct cgccgccaag      60
actggctacg agactgacat gatcgagtcc gacatggagc tcgagactga gctcggcatt    120
gactccatca gcgtgtcga gatcctctcc gaggttcagg ccatgctcaa cgtcgaggcc    180
aaggacgtcg acgctctcag ccgcactcgc actgtgggtg aggtcgtcaa cgccatgaag    240
gctgagatcg ctggtggctc t                                              261

<210> SEQ ID NO 22
<211> LENGTH: 261
<212> TYPE: DNA
<213> ORGANISM: Schizochytrium spp

<400> SEQUENCE: 22
gtctcgaacg agcttcttga aaggccgag accgtcgtca tggaggtcct cgccgccaag      60
actggctacg agactgacat gatcgagtcc gacatggagc tcgagaccga gctcggcatt    120

```
gactccatca agcgtgtcga gattctctcc gaggtccagg ccatgctcaa cgtcgaggcc      180
aaggacgtcg acgctctcag ccgcacccgc actgttggcg aggtcgtcga tgccatgaag      240
gccgagatcg ctggtggctc t                                                261
```

<210> SEQ ID NO 23
<211> LENGTH: 261
<212> TYPE: DNA
<213> ORGANISM: Schizochytrium spp

<400> SEQUENCE: 23

```
gtctcgagcg agcttctcga gaaggccgag actgtcgtca tggaggtcct cgccgccaag      60
actggctacg agactgacat gatcgagtcc gacatggagc tcgagaccga gctcggcatt      120
gactccatca agcgtgtcga gattctctcc gaggtccagg ccatgctcaa cgtcgaggcc      180
aaggacgtcg acgctctcag ccgcacccgc actgttggcg aggtcgtcga tgccatgaag      240
gccgagatcg ctggtggctc t                                                261
```

<210> SEQ ID NO 24
<211> LENGTH: 261
<212> TYPE: DNA
<213> ORGANISM: Schizochytrium spp

<400> SEQUENCE: 24

```
gtctcgagcg agcttctcga gaaggccgag actgtcgtca tggaggtcct cgccgccaag      60
actggctacg agactgacat gattgagtcc gacatggagc tcgagaccga gctcggcatt      120
gactccatca agcgtgtcga gattctctcc gaggttcagg ccatgctcaa cgtcgaggcc      180
aaggacgtcg acgctctcag ccgcactcgc actgttggtg aggtcgtcga tgccatgaag      240
gctgagatcg ctggcagctc c                                                261
```

<210> SEQ ID NO 25
<211> LENGTH: 261
<212> TYPE: DNA
<213> ORGANISM: Schizochytrium spp

<400> SEQUENCE: 25

```
gtctcgaacg agcttctcga gaaagccgag actgtcgtca tggaggtcct cgccgccaag      60
actggctacg agactgacat gatcgagtcc gacatggagc tcgagactga gctcggcatt      120
gactccatca agcgtgtcga gatcctctcc gaggttcagg ccatgctcaa cgtcgaggcc      180
aaggacgtcg atgccctcag ccgcacccgc actgttggcg aggttgtcga tgccatgaag      240
gccgagatcg ctggtggctc t                                                261
```

<210> SEQ ID NO 26
<211> LENGTH: 261
<212> TYPE: DNA
<213> ORGANISM: Schizochytrium spp

<400> SEQUENCE: 26

```
gtctcgaacg agcttctcga gaaggccgag actgtcgtca tggaggtcct cgccgccaag      60
actggctacg agaccgacat gatcgagtcc gacatggagc tcgagaccga gctcggcatt      120
gactccatca agcgtgtcga gattctctcc gaggttcagg ccatgctcaa cgtcgaggcc      180
aaggacgtcg atgctctcag ccgcactcgc actgttggcg aggtcgtcga tgccatgaag      240
gctgagatcg ccggcagctc c                                                261
```

```
<210> SEQ ID NO 27
<211> LENGTH: 261
<212> TYPE: DNA
<213> ORGANISM: Schizochytrium spp

<400> SEQUENCE: 27
gtctcgagcg agcttctcga aaggccgag accgtcgtca tggaggtcct cgccgccaag       60
actggctacg agactgacat gattgagtcc gacatggagc tcgagactga gctcggcatt      120
gactccatca agcgtgtcga gatcctctcc gaggttcagg ccatgctcaa cgtcgaggcc      180
aaggacgtcg atgccctcag ccgcacccgc actgttggcg aggttgtcga tgccatgaag      240
gccgagatcg ctggtggctc t                                                261

<210> SEQ ID NO 28
<211> LENGTH: 261
<212> TYPE: DNA
<213> ORGANISM: Schizochytrium spp

<400> SEQUENCE: 28
gtctcgaacg agcttcttga aaggccgag accgtcgtca tggaggtcct cgccgccaag       60
actggctacg agaccgacat gatcgagtcc gacatggagc tcgagaccga gctcggcatt      120
gactccatca agcgtgtcga gattctctcc gaggttcagg ccatgctcaa cgtcgaggcc      180
aaggacgtcg acgctctcag ccgcactcgc actgttggcg aggtcgtcga tgccatgaag      240
gctgagatcg ctggtggctc t                                                261

<210> SEQ ID NO 29
<211> LENGTH: 51
<212> TYPE: DNA
<213> ORGANISM: Artificial Sequence
<220> FEATURE:
<223> OTHER INFORMATION: Reverse Translation of portion of Repeat 1

<400> SEQUENCE: 29
gtgagcaacg aactgctgga aaaagcggaa accgtggtga tggaagtgct g               51

<210> SEQ ID NO 30
<211> LENGTH: 17
<212> TYPE: PRT
<213> ORGANISM: Artificial Sequence
<220> FEATURE:
<223> OTHER INFORMATION: Translation of SEQ ID NO:29

<400> SEQUENCE: 30

Val Ser Asn Glu Leu Leu Glu Lys Ala Glu Thr Val Val Met Glu Val
1               5                   10                  15

Leu

<210> SEQ ID NO 31
<211> LENGTH: 51
<212> TYPE: DNA
<213> ORGANISM: Artificial Sequence
<220> FEATURE:
<223> OTHER INFORMATION: B. napus optimized rpt1 coding sequence

<400> SEQUENCE: 31
gttagtaacg agcttcttga aaggccgaa accgtcgtga tggaggtcct c                51

<210> SEQ ID NO 32
<211> LENGTH: 51
<212> TYPE: DNA
<213> ORGANISM: Artificial Sequence
```

<220> FEATURE:
<223> OTHER INFORMATION: B. napus optimized rpt1 coding sequence

<400> SEQUENCE: 32
gtctctaacg aacttctcga aaaggctgag acagtcgtga tggaggtgct c    51

<210> SEQ ID NO 33
<211> LENGTH: 51
<212> TYPE: DNA
<213> ORGANISM: Artificial Sequence
<220> FEATURE:
<223> OTHER INFORMATION: B. napus optimized rpt1 coding sequence

<400> SEQUENCE: 33
gttagtaacg agctcttgga gaaagctgag acggttgtca tggaagtgct c    51

<210> SEQ ID NO 34
<211> LENGTH: 51
<212> TYPE: DNA
<213> ORGANISM: Artificial Sequence
<220> FEATURE:
<223> OTHER INFORMATION: B. napus optimized rpt1 coding sequence

<400> SEQUENCE: 34
gttagcaatg aactccttga gaaagcggag actgttgtca tggaggtcct t    51

<210> SEQ ID NO 35
<211> LENGTH: 51
<212> TYPE: DNA
<213> ORGANISM: Artificial Sequence
<220> FEATURE:
<223> OTHER INFORMATION: B. napus optimized rpt1 coding sequence

<400> SEQUENCE: 35
gtgagcaacg agctgcttga aaaggctgaa acagtcgtta tggaggtgtt g    51

<210> SEQ ID NO 36
<211> LENGTH: 51
<212> TYPE: DNA
<213> ORGANISM: Artificial Sequence
<220> FEATURE:
<223> OTHER INFORMATION: B. napus optimized rpt1 coding sequence

<400> SEQUENCE: 36
gtgtctaacg agctcttgga gaaagcagaa acggtcgtca tggaggtgct t    51

<210> SEQ ID NO 37
<211> LENGTH: 51
<212> TYPE: DNA
<213> ORGANISM: Artificial Sequence
<220> FEATURE:
<223> OTHER INFORMATION: B. napus optimized rpt1 coding sequence

<400> SEQUENCE: 37
gtcagtaatg aactcttgga aaaggcggag accgtggtca tggaggtttt g    51

<210> SEQ ID NO 38
<211> LENGTH: 51
<212> TYPE: DNA
<213> ORGANISM: Artificial Sequence
<220> FEATURE:
<223> OTHER INFORMATION: B. napus optimized rpt1 coding sequence

<400> SEQUENCE: 38
gtgtccaatg agctccttga gaaggctgag actgtggtca tggaggttct t    51

<210> SEQ ID NO 39
<211> LENGTH: 51
<212> TYPE: DNA
<213> ORGANISM: Artificial Sequence
<220> FEATURE:
<223> OTHER INFORMATION: B. napus optimized rpt1 coding sequence

<400> SEQUENCE: 39
gtgagtaacg agttgctcga gaaagctgag acagttgtta tggaagttct g         51

<210> SEQ ID NO 40
<211> LENGTH: 51
<212> TYPE: DNA
<213> ORGANISM: Artificial Sequence
<220> FEATURE:
<223> OTHER INFORMATION: B. napus optimized rpt1 coding sequence

<400> SEQUENCE: 40
gtctctaacg aactgcttga gaaggctgaa accgttgtca tggaagtgct t         51

<210> SEQ ID NO 41
<211> LENGTH: 261
<212> TYPE: DNA
<213> ORGANISM: Artificial Sequence
<220> FEATURE:
<223> OTHER INFORMATION: Diverged B. napus optimized rpt1 coding
      sequence

<400> SEQUENCE: 41
gtgtccaacg agttgcttga gaaagctgag acagttgtga tggaggttct cgctgccaag    60
actggatacg aaacagacat gattgaggcg gacatggagc ttgagactga gttgggaatt   120
gacagcatca gagggttga aattctttct gaagtccaag ctatgcttaa cgttgaggcg   180
aaagatgttg atgctctctc taggacgaga acagtgggtg aagttgtcaa cgctatgaag   240
gcagaaatcg ctggttcttc c                                            261

<210> SEQ ID NO 42
<211> LENGTH: 261
<212> TYPE: DNA
<213> ORGANISM: Artificial Sequence
<220> FEATURE:
<223> OTHER INFORMATION: Diverged B. napus optimized rpt2 coding
      sequence

<400> SEQUENCE: 42
gtttctaatg agctgctcga aaaggcagaa actgttgtga tggaagtcct tgctgccaaa    60
actggctacg aaactgacat gatagaatca gacatggagc ttgagacgga gcttggaatt   120
gattccatca gcgtgtgga atcctcagt gaagtccaag ccatgctcaa tgtggaagct   180
aaggatgtgg atgctctctc aaggaccaga actgtcggtg aggttgtcaa tgccatgaag   240
gctgagatag ctggaggctc c                                            261

<210> SEQ ID NO 43
<211> LENGTH: 261
<212> TYPE: DNA
<213> ORGANISM: Artificial Sequence
<220> FEATURE:
<223> OTHER INFORMATION: Diverged B. napus optimized rpt3 coding
      sequence

<400> SEQUENCE: 43
gtctcaaacg aactccttga aaaagctgag accgtcgtga tggaggtctt ggcagctaaa    60

```
accggctatg agactgacat gattgagtct gacatggaat tggagacaga acttgggata    120
gacagcatca aacgtgttga aatcctcagt gaggtccaag ctatgctgaa cgtggaagcg    180
aaggatgttg atgctctgtc cagaacgagg accgttggtg aggttgtgga tgccatgaag    240
gctgaaattg ctggagggtc t                                              261

<210> SEQ ID NO 44
<211> LENGTH: 261
<212> TYPE: DNA
<213> ORGANISM: Artificial Sequence
<220> FEATURE:
<223> OTHER INFORMATION: Diverged B. napus optimized rpt4 coding
      sequence

<400> SEQUENCE: 44
gtttcttcag aactcttgga gaaggctgag acggttgtga tggaggtttt ggctgcaaag     60
actggctatg agaccgacat gattgaatct gatatggaat tggagacaga gcttgggatc    120
gattccatca aaagagtgga gatcctgagt gaagtccaag ccatgctcaa tgttgaagct    180
aaggatgttg atgcactttc aagaacaagg acagtgggtg aggttgtgga tgccatgaag    240
gcggagattg ctggagggag c                                              261

<210> SEQ ID NO 45
<211> LENGTH: 261
<212> TYPE: DNA
<213> ORGANISM: Artificial Sequence
<220> FEATURE:
<223> OTHER INFORMATION: Diverged B. napus optimized rpt5 coding
      sequence

<400> SEQUENCE: 45
gtttcatccg aactcctgga aaaggccgag acggttgtga tggaggtgct cgcagctaag     60
actggttacg agaccgacat gattgaaagt gacatggagc ttgaaaccga gttgggaata    120
gatagcatca aacgtgttga aatcttgtct gaggtccaag ctatgttgaa cgtggaggca    180
aaagatgtcg atgcgctttc aagaaccaga acagtcggtg aggtcgtgga cgccatgaag    240
gctgaaattg ccggaagctc t                                              261

<210> SEQ ID NO 46
<211> LENGTH: 261
<212> TYPE: DNA
<213> ORGANISM: Artificial Sequence
<220> FEATURE:
<223> OTHER INFORMATION: Diverged B. napus optimized rpt6 coding
      sequence

<400> SEQUENCE: 46
gtcagcaatg agttgctgga gaaagccgaa acagttgtga tggaagtcct tgctgcaaaa     60
actggttacg aaacggacat gattgagtca gacatggaat tggagaccga acttggaata    120
gattccatca agagagtgga gatcctctct gaggtgcaag ccatgctcaa cgttgaggct    180
aaagatgttg atgcactcag taggacaaga actgtggggg aagttgtcga tgcgatgaag    240
gctgagattg ctggaggctc t                                              261

<210> SEQ ID NO 47
<211> LENGTH: 261
<212> TYPE: DNA
<213> ORGANISM: Artificial Sequence
<220> FEATURE:
<223> OTHER INFORMATION: Diverged B. napus optimized rpt7 coding
      sequence
```

<400> SEQUENCE: 47

```
gtcagcaacg aattgcttga gaaggctgaa acagttgtca tggaagtgct ggctgcaaaa      60
accggctatg agactgacat gattgagtct gacatggaac ttgagacgga attgggcatt     120
gacagcatca agcgtgttga gatcctcagt gaagtccaag caatgctcaa tgtggaggct     180
aaggatgtgg atgccctctc aaggaccaga acagttggtg aggtcgttga tgcgatgaag     240
gcggagatcg ctggaagttc c                                                261
```

<210> SEQ ID NO 48
<211> LENGTH: 261
<212> TYPE: DNA
<213> ORGANISM: Artificial Sequence
<220> FEATURE:
<223> OTHER INFORMATION: Diverged B. napus optimized rpt8 coding
      sequence

<400> SEQUENCE: 48

```
gtctcctcag aactcctgga aaaggctgag acagttgtga tggaagtcct tgctgcgaaa      60
actggctatg agaccgacat gattgaatct gacatggaac tggagaccga gcttggaatt     120
gactccatca acgtgttgaa atcctctct gaggttcaag cgatgttgaa tgtggaggcc      180
aaagatgttg atgctctttc cagaacaagg acggtgggag aggtggttga tgccatgaag     240
gctgagatag ctgggggttc t                                                261
```

<210> SEQ ID NO 49
<211> LENGTH: 261
<212> TYPE: DNA
<213> ORGANISM: Artificial Sequence
<220> FEATURE:
<223> OTHER INFORMATION: Diverged B. napus optimized rpt9 coding
      sequence

<400> SEQUENCE: 49

```
gtcagcaacg aactccttga aaagctgaa actgttgtga tggaggtttt ggctgcaaag      60
actggatacg agactgacat gatagagtca gacatggagt tggaaacaga gcttgggatt     120
gatagcatca agcgtgtgga atcctttct gaggttcaag ccatgctgaa cgttgaggcc      180
aaagatgtcg atgctttgtc aaggaccaga acggttggag aagtggtcga tgccatgaag     240
gctgagatag ctggtggatc a                                                261
```

<210> SEQ ID NO 50
<211> LENGTH: 9
<212> TYPE: PRT
<213> ORGANISM: Artificial Sequence
<220> FEATURE:
<223> OTHER INFORMATION: Tandem oligopeptide repeat

<400> SEQUENCE: 50

```
Ala Glu Pro Ala Glu Pro Ala Glu Pro
1               5
```

<210> SEQ ID NO 51
<211> LENGTH: 5
<212> TYPE: PRT
<213> ORGANISM: Artificial Sequence
<220> FEATURE:
<223> OTHER INFORMATION: Polyglutamine repeat

```
<400> SEQUENCE: 51

Gln Gln Gln Ala Gln
1               5
```

PROCESS FOR DESIGNING DIVERGED, CODON-OPTIMIZED LARGE REPEATED DNA SEQUENCES

PRIORITY CLAIM

This application claims the benefit of the filing date of U.S. Provisional Patent Application Ser. No. 61/672,114, filed Jul. 16, 2012, for "PROCESS FOR DESIGNING DIVERGED, CODON-OPTIMIZED LARGE REPEATED DNA SEQUENCES."

TECHNICAL FIELD

The present disclosure relates generally to methods for optimizing gene expression. In particular embodiments, the disclosure relates to methods for optimizing the expression of gene products having amino acid repeat domains.

BACKGROUND

Advances in chemical DNA synthesis technologies have brought the expense of total gene synthesis to a level that is frequently more cost advantageous than attempts to clone the gene from its native source. Thus, the computer-aided design of synthetic DNA sequences that encode valuable proteins is becoming increasingly important in the field of plant transformation and other areas of biotechnology.

The genetic code consists of three-nucleotide units called codons. There are 64 possible codons, each specifying one of twenty amino acids or an end to translation ("STOP codons"). Therefore, at least some codons are redundant. In the coding system used by the vast majority of organisms, two amino acids are each encoded by a single codon, whereas all other amino acids are separately encoded by two, three, four, or six codons, with three STOP codons. For amino acids represented by two, three, or four codons, the codons differ from each other at the third nucleotide position. For amino acids represented by two codons, the third position is either a purine (A, G) or pyrimidine (C, T) in both cases. For the three amino acids that are represented by six codons (Arg, Leu, and Ser), each has one block of four codons that follows this pattern by differing in the third position, plus one additional set of two codons. Arg and Leu are each represented by a two-codon block different from each other by a change in the first and second nucleotide positions. The two-codon representation of serine (Ser) is different from that of the Arg two-codon block only in the third nucleotide position.

For a particular amino acid, a given organism does not use the possible codons equally. Organisms each have a bias in codon usage. The pattern of bias in codon usage is distinct for an organism and its close relatives throughout the genome. For example, in *Streptomyces* spp., frequent codons generally include G or C in the third nucleotide position. Rare codons generally include A or T in the third position. In other organisms, A or T is preferred in the third position. Within a particular species, there can be distinct categories of genes with their own codon bias. In *E. coli*, for example, there are roughly three classes of genes, each with a distinctive codon usage signature. One class is rich in important proteins that are abundantly expressed; the second class includes proteins that are expressed at relatively low levels; and the third class includes proteins likely to have been recently acquired from other species.

In most synthetic gene design strategies, the process attempts to match the codon composition of a synthetic gene to the codon compositions of genes of a host in which the synthetic gene will be expressed. See, e.g., U.S. Patent Publication No. US2007/0292918 A1. Such strategies may in some situations lead to increased expression of the synthetic gene in the host. For example, codon optimization in yeast may significantly improve the translation of heterologous gene transcripts due to minimizing the effects of, e.g., limiting aminoacyl-tRNAs and transcription termination at AT-rich sequences. See, e.g., Daly and Hearn (2004) J. Mol. Recognition 18:119-38.

However, despite general agreement in the art over the need for some sort of codon optimization, practitioners disagree over the general strategy that should be employed for optimization. One strategy that is preferred by some is to maximize the use of frequent codons in the expression host species during the design of heterologous genes. A second strategy preferred by others is to place maximum value on the context of particular codons, and therefore to maximize the use of codon pairs that occur frequently in the expression host. A third strategy is to make the codon usage of the new coding sequence in the new species resemble the codon usage of the reference coding sequence in the species of origin. This third strategy places high value on the recognition of possible requirements for rare codons to ensure proper secondary structure of transcript RNA molecules. A further strategy is to make the codon composition of the heterologous gene resemble the overall codon composition of expressed genes of the new host. Additionally, simply using the same frequently-occurring codon repeatedly in a heterologous sequence is expected to eventually have the same effect as selecting a rare codon; e.g., overuse of the corresponding tRNA will limit the availability of the tRNA. A person attempting to optimize the codons of a gene sequence for expression in a host organism must balance these strategies and their underlying concerns in order to arrive at a particular methodology.

In addition to yeast and other eukaryotic cells (for example, Chinese Hamster Ovary cells (CHO) cells, Human Embryonic Retinoblast (HER) cells, and Human Embryonic Kidney (HEK) cells), numerous bacteria have been used as host cells for the preparation of heterologous recombinant proteins. One significant disadvantage of numerous bacterial systems is their use of rare codons, which are not preferred in human genes. The use of these rare codons can lead to delayed and reduced expression of recombinant heterologous genes that reflect a different codon usage preference, for example, human genes. Sorensen et al. (2003) J. Chromatography B 786:207-14. To attempt to overcome this disadvantage, a nucleic acid sequence may be modified to encode a recombinant heterologous polypeptide variant, for example, wherein specific codons of the nucleic acid sequence have been changed to codons that are favored by a particular host and can result in enhanced levels of expression. See, e.g., Haas et al. (1996) Curr. Biol. 6:315; and Yang et al. (1996) Nucleic Acids Res. 24:4592. In addition, the reiterative nature of the design process allows the elimination of various sequence motifs, such as intron splice recognition sites, mRNA instability determinants, highly stable stem-loop structures, and restriction enzyme recognition sites from the finished DNA sequence. See, e.g., GENESCRIPT™ product insert. Additionally, genes encoding rare tRNAs can be expressed in a host organism to overcome some of the effects of using rare codons in a heterologous coding sequence. Sorensen et al. (2003), supra.

The process of optimizing the nucleotide sequence coding for a heterologously expressed protein can be an important step for improving expression yields. However, several potential problems limit the usefulness of codon optimization for the expression of particular genes. For example, the secondary structure of a codon-optimized transcript may limit translation of the transcript. Griswold et al. (2003) Protein Expression and Purification 27:134-42. Additionally, there are a number of sequence motifs that are desirably avoided in synthetic sequences for heterologous expression, including class I and II transcriptional termination sites in *E. coli* for a gene under the control of a T7 promoter; Shine-Dalgarno-like sequences; potential splice signals; polyadenylation signals; and sequences that promote ribosomal frameshifts and pauses. Welch et al. (2010) J. R. Soc. Interface 6:S467-76.

The sequences of many proteins include amino acid repeat patterns, including single amino acid repeats and tandem oligopeptide repeats. Katti et al. (2000) Protein Science 9:1203-9. Simple nucleotide sequence repeats originate from unequal crossing-over or replication errors due to formation of DNA secondary structures, such as hairpins or slipped strands. Pearson and Sinden (1998) Curr. Opin. Struct. Biol. 8:321-30. Nucleotide sequence repeats in a coding region may be translated into single amino acid repeats or tandem oligopeptide repeats that may significantly impact protein structure and function. It has been estimated that about 14% of all proteins contain significant internal amino acid repeats, with more amino acid repeats appearing in eukaryotic proteins than in prokaryotic proteins. Marcotte et al. (1999) J. Mol. Biol. 293:151-60. Glutamine, alanine, glycine, glutamic acid, and serine repeats are the most common single amino acid repeats, while long tandem repeats of highly hydrophobic amino acids are rare. Katti et al. (2000), supra; Green and Wang (1994) Proc. Natl. Acad. Sci. USA 91:4298-302.

Proteins including single amino acid repeats include transcription regulatory proteins. Katti et al. (2000), supra. Proteins including tandem oligopeptide repeats include the antigenic proteins from certain protozoan parasites, structural proteins (e.g., proline-rich plant cell wall structural proteins, keratins, trichohyalins, tropoelastins, silk moth fibroins, *drosophila* salivary glue proteins, yeast cell wall proteins, epithelial mucins, and cartilage-specific aggrecan core proteins), skin epidermal keratinocyte proteins, involucrins, loricrins, repetins, cornifins, and neurofilament triplet-H proteins of mammalian neuronal axons. Id. In addition to naturally occurring proteins, some synthetic polypeptides containing repeats may be desirable for production and use in a variety of applications. See, e.g., U.S. Patent Publication No. US 2009/0093621 A1.

Disclosure

Described herein are methods that may be used to design synthetic nucleic acid molecules encoding a polypeptide comprising at least one repeated amino acid sequence region. Repeated amino acid sequence regions may be, for example, single amino acid repeats or tandem oligopeptide repeats. In embodiments, multiple, substantially-diverged synthetic nucleic acid sequences may be designed within the constraints of predetermined gene design parameters. Synthetic nucleic acid sequences may be designed from a reference nucleic acid sequence, for example, to optimize heterologous expression of the nucleic acid sequence in a host organism. Alternatively, synthetic nucleic acid sequences may be designed de novo to encode a desired polypeptide. For a review of polypeptide design, see, e.g., Protein Design, Eds. Raphael Guerois and Manuela Lopez de la Paz, 2006, Humana Press, Totowa, N.J.

In embodiments, the method may comprise providing a nucleic acid sequence encoding a polypeptide comprising at least one amino acid repeat region. In some embodiments, a nucleic acid sequence encoding a polypeptide comprising at least one amino acid repeat region may be provided by determining a nucleic acid sequence encoding a polypeptide comprising at least one amino acid repeat region in an organism (for example, by cloning of the nucleic acid sequence or by extracting the sequence from a sequence database). In particular embodiments, at least one nucleic acid sequence(s) encoding an amino acid repeat region of the polypeptide may then be extracted, each as a separate sequence, from the provided nucleic acid sequence.

In some embodiments, an extracted nucleic acid sequence encoding an amino acid repeat region may be imported (e.g., individually imported) into a computer-implemented software program that is capable of optimizing a coding sequence according to predetermined parameters. In particular embodiments, the computer-implemented software program may be OPTGENE™ (available from *Ocimum* Biosolutions). A sample amino acid repeat sequence may then be deduced from each extracted nucleic acid sequence, for example, by referring to the standard genetic code. In particular embodiments, a sample amino acid repeat sequence may be deduced from each extracted nucleic acid sequence by a computer-implemented software program. In further embodiments, a sample amino acid repeat sequence may be directly imported into a computer-implemented software program, for example, by importing into the computer-implemented software program the amino acid sequence of an amino acid repeat region in the polypeptide of interest.

In other embodiments, a sample amino acid repeat sequence may be used to deduce a plurality of sample codon-optimized nucleic acid sequences encoding the amino acid repeat region (for example, by independently deducing a plurality of different sample codon-optimized nucleic acid sequences encoding the amino acid repeat region from the sample amino acid repeat sequence according to redundancy of the genetic code and an appropriate codon usage table). In embodiments utilizing a computer-implemented software program, sample codon-optimized nucleic acid sequences encoding an amino acid repeat region may each be exported into a text file or otherwise recorded for the practitioner. In embodiments wherein a synthetic nucleic acid molecule is designed to optimize a reference nucleic acid molecule comprising at least one repeated amino acid sequence region, the steps of deducing a sample amino acid repeat sequence and deducing sample codon-optimized nucleic acid sequences encoding the amino acid repeat region may be carried out for each and every amino acid repeat region of a polypeptide encoded by the reference nucleic acid molecule.

In further embodiments, sample codon-optimized nucleic acid sequences encoding amino acid repeat regions may be aligned by sequence homology. In particular embodiments, all of the sample codon-optimized nucleic acid sequences encoding an amino acid repeat region obtained for all of the repeated amino acid sequence regions in a reference nucleic acid molecule may be aligned to each other by sequence homology. In certain embodiments, the sample codon-optimized nucleic acid sequences may be aligned using the CLUSTALW™ program, Mega 3.1. A neighbor-joining tree may be assembled for the aligned sample sequences. A single sample codon-optimized nucleic acid sequence encoding the amino acid repeat region may be selected for each repeated amino acid sequence region from a deeply-branched section of the neighbor-joining tree.

In these and further embodiments, a selected coding sequence for a repeated amino acid sequence may be incorporated into a codon-optimized nucleic acid sequence encoding a polypeptide of interest to produce an expression-optimized nucleic acid sequence. In particular embodiments, the selected coding sequence may be incorporated at the desired position for the corresponding amino acid repeat unit in the polypeptide of interest, so as to maintain the correct reading frame for the complete polypeptide coding sequence. In some embodiments, further analysis may be performed upon a codon-optimized sequence, for example, to confirm the absence of undesired nucleic acid motifs (e.g., nucleic acid motifs forming undesirable secondary structure in an RNA molecule transcribed therefrom), confirm the absence of restriction enzyme recognition sites, and/or assure codon and sequence diversity.

In some embodiments, a method of the invention may be used to design a synthetic nucleic acid sequence that encodes a heterologous or endogenous polypeptide of interest. In some of these embodiments, the synthetic nucleic acid sequence may be optimized for expression in a host organism, for example, by codon-optimization to reflect the codon usage of the expression host. In particular embodiments, a synthetic nucleic acid sequence is designed that has been optimized for heterologous expression in a plant cell; e.g., *Brassica napus*. In further embodiments, a synthetic nucleic acid sequence is designed that has been optimized for heterologous expression in a bacterial host cell; e.g., *Pseudomonas fluorescens*. In these and other embodiments, a design process of the invention may be used to design a synthetic nucleic acid sequence that encodes a novel polypeptide of interest comprising amino acid repeat regions.

The foregoing and other features will become more apparent from the following detailed description of several embodiments, which proceeds with reference to the accompanying figures.

BRIEF DESCRIPTION OF THE DRAWINGS

FIG. 2 includes the amino acid sequences of the ten Pro-Ala repeats of *Schizochytrium* PUFA ORFA.

FIG. 3 includes a CLUSTALW™ alignment (in Vector NTI™ software suite) of the amino acid sequences of the 9 oligopeptide repeat domains of *Schizochytrium* spp. (American Type Culture Collection Deposit Number ATTC_20888) PUFA ORFA.

FIG. 4 includes a CLUSTALW™ alignment (in Vector NTI™ software suite) of the native *Schizochytrium* DNA sequences encoding each of the 9 amino acid repeat domains of PUFA ORFA. The alignment demonstrates that the DNA sequences are 100% homologous and 89.7% identical.

FIG. 5 includes a reproduction of a program interface. Shown on the top line of the chart is a portion of a computer-generated sequence that was derived by reverse translation of the amino acid sequence of *Schizochytrium* PUFA ORFA Repeat 1 (SEQ ID NO:11) using a nonbiased standard genetic code, and which sequence is further disclosed as SEQ ID NO:29. On the second line of the chart is shown the amino acid sequence encoded by the sequence of the top line, and which therefore represents a portion of *Schizochytrium* PUFA ORFA Repeat 1 (SEQ ID NO:11) and is set forth in SEQ ID NO:30. The remaining lines show multiple reverse translations of Line 2 using the standard genetic code and a codon usage bias of *Brassica napus*. The third through twelfth lines show "rpt1 nap1" through "rpt1 nap10," respectively. These nucleotide sequences (SEQ ID NOs:31 to 40, respectively) were obtained by reverse translation of SEQ ID NO:30, using the standard genetic code and a codon usage bias of *B. napus*.

FIG. 7 includes Smith-Wasserman homologies of selected *Brassica napus* codon-optimized sequences of repeats of *Schizochytrium* PUFA ORFA.

FIG. 8 includes a CLUSTALW™ alignment (in VECTOR NTI™ software suite) of the redesigned (diverged) DNA sequences encoding each of the 9 repeat domains of *Schizochytrium* PUFA ORFA. The alignment demonstrates that the DNA sequences are 93.1% homologous and 61.7% identical.

SEQUENCE LISTING

Figure 1:
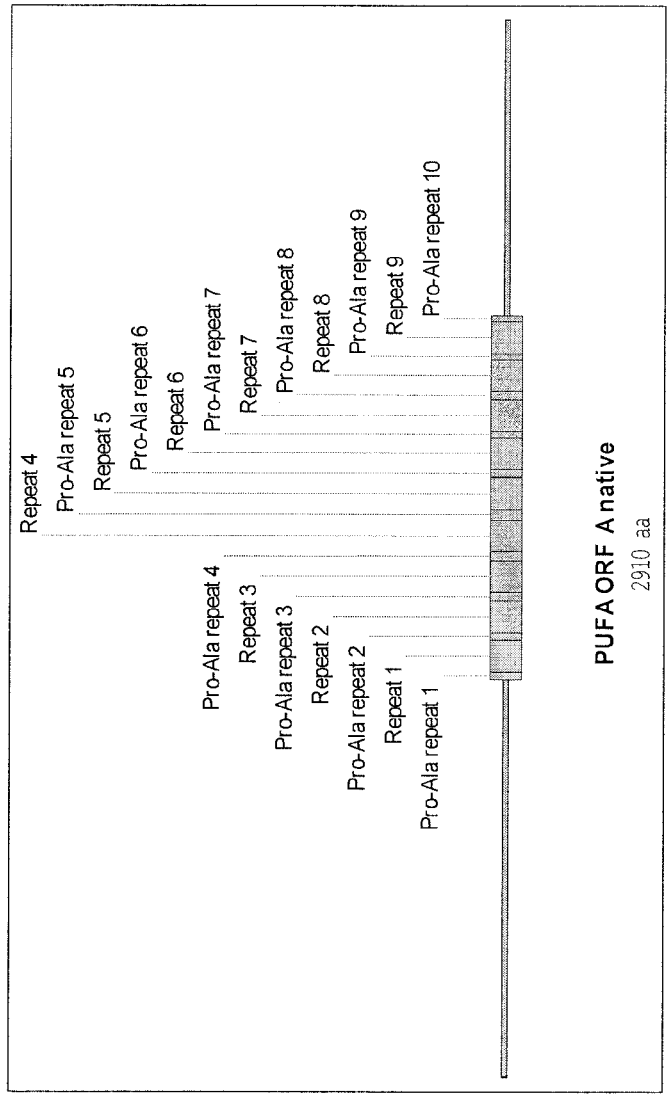
FIG. 1 includes a graphical representation of the protein encoded by *Schizochytrium* PUFA ORFA, including the relative locations of amino acid Repeat domains and flanking Pro-Ala repeats. It is to be noted that the Repeats 1 through 9 are sometimes denoted herein as Repeats A through I, wherein Repeat 1 is sometimes referred to as Repeat A, Repeat 2 as Repeat B, etc.

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood to be included by any reference to the displayed strand. Unless otherwise indicated, nucleic acids are written, left to right, in 5' to 3' orientation.

Amino acids may be referred to herein by either their commonly known three-letter symbols, or by the one-letter symbols recommended by the IUPAC-IUB Biochemical Nomenclature Commission. Amino acid sequences are written, left to right, in amino- to carboxy-orientation. In the accompanying Sequence Listing:

SEQ ID NOs:1-10 show the amino acid sequences of the ten Pro-Ala repeats of *Schizochytrium* PUFA ORFA.

SEQ ID NOs:11-19 show the amino acid sequences of the nine oligopeptide Repeat regions of *Schizochytrium* PUFA ORFA.

SEQ ID NOs:20-28 show the native *Schizochytrium* nucleotide sequences encoding each of the nine oligopeptide repeat regions of PUFA ORFA.

SEQ ID NO:29 shows a DNA sequence that encodes a portion of *Schizochytrium* PUFA ORFA Repeat 1 derived by reverse translation of the amino acid sequence of *Schizochytrium* PUFA ORFA Repeat 1 using a nonbiased standard genetic code.

SEQ ID NO:30 shows the amino acid sequence encoded by SEQ ID NO:29 and represents a portion of *Schizochytrium* PUFA ORFA Repeat 1:

SEQ ID NOs:31-40 show nucleotide sequences obtained by reverse translation of SEQ ID NO:30, using the standard genetic code and the codon usage bias of *Brassica napus*.

SEQ ID NOs:41-49 show exemplary synthetic DNA sequences encoding each of the 9 repeat domains of *Schizochytrium* PUFA ORFA.

SEQ ID NO:50 shows an exemplary tandem oligopeptide repeat comprising 3 repeats of a 3-amino acid sequence.

SEQ ID NO:51 shows an exemplary imperfect polyglutamine repeat

MODE(S) FOR CARRYING OUT THE INVENTION

I. Overview of Several Embodiments

A problem may be encountered during the optimization of a coding sequence for expression in a host organism when the encoded polypeptide contains repeated amino acid domains. Within cloned DNA in bacterial hosts, large regions of closely spaced, highly-homologous nucleotide sequences can contribute to instability; even small, perfect repeats of only 50 bases can be substrates for recombination in *Escherichia coli*. Moreover, these sequences may lead to expression problems when the large repeats are present in transcribed mRNA. For example, transcripts comprising polyglutamine repeats may be unstable, since $(CAG)_n$:$(CTG)_n$ repeats can adopt secondary DNA structures leading to replication errors, repair errors, or recombination. Pearson and Sinden (1998), supra. Polyalanine repeats may also lead to transcript instability. Muragaki et al. (1996) Science 272:548-51.

In view of the foregoing, the dual limitations of codon composition and motif avoidance create gene design problems, since the design of each individual repeated sequence element must conform to the same codon composition and motif avoidance tables used for the gene as a whole, while trying to design DNA sequences for the repeats that are sufficiently diverged to avoid repeated sequence instability problems. Gene design processes are not equipped to accommodate the development of new codon-biased DNA sequences for multiple large amino acid repeats, since all codon choices in an individual repeat must be continually balanced with the codon choices made at the same position in the coding regions corresponding to the other repeats, so as to avoid generating highly related DNA sequences.

The presence of highly-repeated sequence regions in a synthetic nucleic acid molecule also generates technical difficulties in gene synthesis, and in sequence verification of the completed synthetic molecule. These problems may be particularly acute when repeated amino acid domains are larger than only several amino acid residues. In some embodiments of the invention, these problems may be addressed by a method for designing diverged and codon-optimized nucleic acid sequences encoding amino acid repeat regions. Particular embodiments of the methods described herein are universally applicable to the design of any codon-optimized DNA sequence encoding a polypeptide with repeated amino acid domains.

II. Abbreviations dsDNA double-stranded DNA
ssDNA single-stranded DNA
NCBI National Center for Biotechnology Information
PCA polymerase cycling assembly
PCR polymerase chain reaction

III. Terms

Use of the singular forms "a," "an," and "the" include plural references unless the context clearly dictates otherwise. For example, reference to "a polynucleotide" includes a plurality of polynucleotides, reference to "a substrate" includes a plurality of such substrates, reference to "a variant" includes a plurality of such variants, etc.

Where a range of values is recited, it is to be understood that each intervening integer value, and each fraction thereof, between the recited upper and lower limits of that range is also specifically disclosed, along with each sub-range between such values. The upper and lower limits of any range can independently be included in, or excluded from, the range, and each range where either, neither, or both limits are included is also encompassed within the invention. Where a value being discussed has inherent limits (for example, where a component can be present at a concentration of from 0 to 100%, or where the pH of an aqueous solution can range from 1 to 14), those inherent limits are specifically disclosed.

Where a value is explicitly recited, it is to be understood that values which are about the same quantity or amount as the recited value are also within the scope of the invention. Where a combination is disclosed, each subcombination of the elements of that combination is also specifically disclosed, and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly, or in any combination with the other alternatives, are also hereby disclosed (more than one element of an invention can have such exclusions, and all combinations of elements having such exclusions are hereby disclosed).

Unless otherwise provided, all technical and scientific terms used herein have the same meaning as commonly understood by one of ordinary skill in the art of genetics, bioinformatics, and gene design. General dictionaries containing many of the teems used in this disclosure are: Singleton et al. (1994) Dictionary of Microbiology and Molecular Biology, 2nd Ed., John Wiley and Sons, New York; and Hale and Marham (1991) The Harper Collins Dictionary of Biology, Harper Perennial, New York. Any methods and materials similar or equivalent to those described herein may be used in the practice or testing of embodiments of the invention, though certain methods and materials are exemplified by those disclosed herein.

Amino acid repeat: As used herein, the term "amino acid repeat," refers to amino acid sequences within a polypeptide that comprise repeating units of the same amino acid or amino acid(s). Thus, "amino acid repeat" refers to both single amino acid repeats (e.g., Ala-Ala-Ala) and tandem oligopeptide repeats (e.g., Ala-Glu-Pro-Ala-Glu-Pro-Ala-Glu-Pro (SEQ ID NO:50)). An amino acid repeat may be of any length that is repeated in a polypeptide; for example, a single amino acid repeat may be a single residue in length (repeated a number of times), while a tandem oligopeptide repeat may be, e.g., from 2 amino acids in length to about 100 amino acids in length, or more. In particular examples, an oligopeptide repeat may be about 10, about 20, about 30, about 40, about 50, about 60, about 65, about 70, about 80, about 90, about 100, or about 110 amino acids in length; for example, 85 amino acids in length.

The term "amino acid repeat unit" refers to contiguous amino acids that make up an amino acid repeat. It is not necessary for every amino acid in an amino acid repeat unit to be the amino acid predicted at its position by the overall pattern of the repeat. For example, a polyglutamine amino acid repeat unit may include the sequence, "Gln-Gln-Gln-Ala-Gln" (SEQ ID NO:51), and the entire sequence may be considered a polyglutamine repeat, notwithstanding the presence of an alanine in the contiguous sequence.

Codon usage bias: As used herein, the term "codon usage bias," or simply "codon usage," refers to the high-frequency preferential use of a particular codon (as opposed to other, synonymous codons) coding for an amino acid within an organism. A codon usage bias may be expressed as a quantitative measurement of the rate at which a particular codon is used in the genome of a particular organism, for example, when compared to other codons that encode the same amino acid.

Various methods are known to those of skill in the art for determining codon usage bias. In some embodiments, codon usage bias may be determined by the codon adaptation index (CAI) method, which is essentially a measurement of the distance of a gene's codon usage to the codon usage of a predefined set of highly-expressed genes. Sharp and Li (1987) Nucleic Acids Res. 15:1281-95. Alternative methods for determining a codon usage bias include MILC (measure independent of length and composition) (Supek and Vlahovicek (2005) BMC Bioinformatics 6:182) and relative synonymous codon usage (RSCU), which is the observed frequency of a particular codon divided by the frequency expected from equal usage of all the synonymous codons for that amino acid. Sharp et al. (1986) Nucleic Acids Res. 14:5125-43. RSCU values close to 1.0 indicate a lack of bias for the particular codon, whereas departure from 1.0 reflects codon usage bias.

Thus, codon usage bias includes the relative frequencies of use of codons that encode the same amino acid ("synonymous codons"). A bias may be naturally occurring; for example, the codon bias in an organism's genome reflects the relative overall use of synonymous codons within all the genes in that organism. A bias may also be used in a computational algorithm, where, for example, it may be used to determine the relative frequency with which different synonymous codons are selected for use in designing a polynucleotide sequence. Similarly, the "relative" frequency of any sequence element used to encode a polypeptide within a nucleotide sequence is the frequency with which that sequence element is used to encode a feature of the polypeptide, divided by the number of occurrences within the polypeptide in a given reading frame of features that could be encoded by that sequence element.

Codon usage bias may also be inferred from a codon usage table for a particular expression host organism. Codon usage tables are readily available for many expression host organisms. See, e.g., Nakamura et al. (2000) Nucleic Acids Res. 28:292 (Codon Usage Database—updated versions available at kazusa.or.jp/codon). When a codon usage table is not available, it may be assembled from public organismal genetic databases, such as those maintained by NCBI (available at ncbi.nlm.nih.gov/sites/genome). In some embodiments, a codon usage table may be assembled from a set of coding regions obtained from the particular expression host organism. In some examples, a set of coding regions comprises at least 100, at least 200, at least 300, at least 400, at least 500, at least 550, at least 600, or more coding regions obtained from the particular expression host organism.

The terms "codon usage table," or "codon bias table," or "codon frequency table" are used interchangeably and describe a table which correlates each codon that may be used to encode a particular amino acid with the frequencies with which each codon is used to encode that amino acid in a specific organism, within a specified class of genes within that organism, or within one or more synthetic polynucleotides.

Absolute codon frequency: As used herein, the term "absolute codon frequency" refers to the frequency with which a codon appears relative to the total number of codons (e.g., both synonymous and non-synonymous codons) within a polynucleotide or set of polynucleotides in a given reading frame (e.g., a reading frame that is used to encode a polypeptide of interest). Similarly, the "absolute" frequency of any sequence element used to encode a polypeptide within a polynucleotide is the frequency with which that sequence element is used to encode a feature (e.g., amino acid, amino acid pair, etc.) of the polypeptide, divided by the number of occurrences within the polypeptide of features of the same size as those that could be encoded by that sequence element.

Codon space: As used herein, the term "codon space" refers to all of the possible polynucleotide sequences that can be used to encode a specific polypeptide, by varying the codons used to encode amino acids within the polypeptide.

Codon substitution: As used herein, the term "codon substitution" refers to the altering of a nucleotide coding sequence by changing one or more of the codons encoding one or more amino acids of an encoded polypeptide, without altering the amino acid sequence of the encoded polypeptide.

Codon optimization: As used herein, the term "codon optimization" refers to processes employed to modify an existing coding sequence, or to design a coding sequence in the first instance, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. Codon optimization also includes, for example, the process sometimes referred to as "codon harmonization," wherein codons of a codon sequence that are recognized as low-usage codons in the source organism are altered to codons that are recognized as low-usage in the new expression host. This process may help expressed polypeptides to fold normally by introducing natural and appropriate pauses during translation/extension. Birkholtz et al. (2008) Malaria J. 7:197-217.

Modify: As used herein, the terms "modify" or "alter," or any forms thereof, mean to modify, alter, replace, delete, substitute, remove, vary, or transform.

Neighbor joining tree: As used herein, the term "neighbor joining tree" refers to a bottom-up clustering method used for the construction of phylogenetic trees. In examples, an algorithm (e.g., the CLUSTAL™ algorithm) creates a tree from pairwise distances between sequences, for example, as calculated by the Needleman-Wunsch algorithm. This tree ("the guide tree") may be used as a guide for aligning the multiple sequences in the tree. A discussion on the construction and interpretation of neighbor-joining trees may be found in Kumir and Gadagker, (2000) J. Molec. Evol. 51:544-53.

Phylogenetic trees may be calculated from a multiple alignment by methods known to those of skill in the art, e.g., the Neighbor-Joining method of Saitou and Nei based on a matrix of "distances" between the sequences. These distances may be corrected for "multiple hits." This correction stretches distances to at least partially correct for underestimation by the mean number of differences of the actual number of differences at each position that occurred during evolution. Detailed information regarding neighbor joining trees, and methods of their construction, may be found, for example, in Kao (Ed.) Encyclopedia of Algorithms (2008), Springer, New York.

Nucleic acid molecule: As used herein, the term "nucleic acid molecule" refers to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides, linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example: labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including for example: single-stranded, double-stranded, partially duplexed, triplexed, hairpinned, circular, and padlocked conformations.

Protein/polypeptide: The teams "protein" and "polypeptide" are used interchangeably herein. The terms refer to a contiguous molecular chain of amino acids linked through peptide bonds. The teens do not refer to a specific length of the product. Thus, "peptides," "oligopeptides," and "proteins" are included within the definition of polypeptide. The terms include polypeptides containing co- and/or post-translational modifications of the polypeptide made in vivo or in vitro; for example and without limitation: glycosylations, acetylations, phosphorylations, PEGylations and sulphations. In addition, protein fragments, analogs (including amino acids not encoded by the genetic code: e.g., homocysteine, ornithine, p-acetylphenylalanine, D-amino acids, and creatine), natural or artificial mutants, variants, fusion proteins, derivatized residues (e.g., alkylation of amine groups, acetylations or esterifications of carboxyl groups), and combinations of any of the foregoing are included within the meaning of polypeptide.

Typically, proteins have a function. However, proteins also encompass oligopeptides and smaller contiguous amino acid sequences that do not have a functional activity. Non-limiting examples of functional proteins include: receptors, receptor ligands, cytokines, antibodies, immunomodulatory molecules, signalling molecules, fluorescent proteins, proteins with insecticidal or biocidal activities, and enzymes. Useful general classes of enzymes include, but are not limited to: proteases, cellulases, oxidoreductases, lipases, lyases, ligases, hemicellulases, laccases, amylases, glucoamylases, esterases, dehydrogenases, lactases, polygalacturonases, galactosidases, ligninases, oxidases, peroxidases, transferases, glucose isomerases, nitrilases, hydroxylases, hydrolases, polymerases and depolymerases. In addition to enzymes, proteins that can be encoded by synthetic nucleic acid molecules disclosed herein include without limitation: transcription factors, antibodies, receptors, growth factors (any of the PDGFs, EGFs, FGFs, SCF, HGF, TGFs, TNFs, insulin, IGFs, LIFs, oncostatins, CSFs, etc.), immunomodulators, peptide hormones, cytokines, integrins, interleukins, adhesion molecules, thrombomodulatory molecules, protease inhibitors, angiostatins, defensins, cluster of differentiation antigens, interferons, chemokines, antigens including those from infectious viruses and organisms, oncogene products, thrombopoietin, erythropoietin, tissue plasminogen activator, and any other biologically active protein which is desired for use in a clinical, diagnostic, or veterinary setting. All of these proteins are well-defined in the literature (for example, by exemplary amino acid sequences), and are so defined herein. Also included are deletion mutants of such proteins, individual domains of such proteins, fusion proteins made from such proteins, and mixtures of such proteins.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

In particular embodiments, nucleic acid coding sequences may be compared to determine sequence identity. In these and other embodiments, coding sequences may be aligned without allowing additions or deletion (i.e., gaps).

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10. Alternatively, optimal alignment of sequences for comparison may be conducted using the MEGALIGN™ program in the LASERGENE™ suite of bioinformatics software (DNASTAR, Inc.), using default parameters. This program embodies several alignment schemes described in the following references: Dayhoff (1978) A model of evolutionary change in proteins—Matrices for detecting distant relationships. In Dayhoff (ed.) Atlas of Protein Sequence and Structure, National Biomedical Research Foundation, Washington D.C. Vol. 5, Suppl. 3, pp. 345 358; Hein (1990) Methods Enzymol. 183:626-45; Higgins and Sharp (1989), supra; Myers and Muller (1988) CABIOS 4:11-7; Robinson (1971) Comb. Theor 11:105; Santou and Nes (1987) Mol. Biol. Evol. 4:406-25; Sneath and Sokal (1973) Numerical Taxonomy—the Principles and Practice of Numerical Taxonomy, Freeman Press, San Francisco, Calif.; and Wilbur and Lipman (1983) Proc. Natl. Acad. Sci. USA 80:726-30.

The NCBI Basic Local Alignment Search Tool (BLAST™; Altschul et al. (1990)) is available from several sources, including NCBI (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Synthetic: As used herein in reference to a nucleotide sequence (or nucleic acid molecule comprising a synthetic nucleotide sequence), the term "synthetic" refers to a sequence that is designed (e.g., in silico), for example, for the purpose of expressing an encoded polypeptide of interest. The term "synthetic nucleotide" also includes the product of the manufacture of a nucleic acid molecule by means of chemically synthesized oligonucleotides by in vitro or in vivo methodologies known to those skilled in the art of gene synthesis, or by combinations of in vitro or in vivo methods.

IV. Diverged and Codon-Optimized Nucleic Acid Sequences Encoding Amino Acid Repeat Regions This disclosure provides methods for designing a diverged, codon-optimized nucleic acid sequence. In some embodiments, methods of the invention may be used to design a nucleic acid sequence encoding a polypeptide of interest, wherein the polypeptide of interest comprises at least one amino acid repeat region. In certain embodiments, the polypeptide of interest may comprise a plurality of amino acid repeat regions. Each amino acid repeat region may comprise one or more amino acid repeat units. Polypeptides encoded by sequences comprising diverged, codon-optimized nucleic acid sequences that are designed by methods of the invention may comprise in some embodiments amino acid repeat regions of, for example, 10 to 300 amino acids in length. In embodiments, use of the present method avoids certain problems normally associated with synthetic nucleotide sequences that encode polypeptides with amino acid repeat regions. In some embodiments, problems avoided by the use of disclosed methods may include: transcript instability; heterologous gene instability; relatively low expression; inefficient gene synthesis; and inefficient gene sequencing.

In some embodiments, only a coding region of a nucleic acid molecule is designed using processes according to the disclosure. However, in some embodiments, it may be desirable to include certain non-coding sequences either upstream, downstream, or within (e.g., introns) a coding sequence. Therefore, in some embodiments, the sequence(s) of any non-coding sequences included in a nucleic acid molecule comprising a synthetic coding sequence as described may be taken account in methods of the disclosure.

In some embodiments, a synthetic nucleic acid sequence encoding a polypeptide comprising at least one amino acid repeat unit is provided. A method for designing a diverged, codon-optimized nucleic acid sequence that encodes a polypeptide of interest generally begins with a desired polypeptide or gene product to be expressed. Alternatively, the process may begin with a gene or nucleic acid sequence with a known or unknown function. For example, the process may be used to design a synthetic nucleic acid sequence to express a polypeptide, e.g., to investigate the function of a polypeptide encoded by the nucleic acid sequence. In some embodiments, a polypeptide of interest may be designed or derived from a reference amino acid sequence of interest; for example, a reference protein or reference protein domain. In other embodiment, a polypeptide of interest may be designed de novo; for example, to obtain certain biochemical or biophysical properties expected for a molecule with a particular amino acid sequence, or to obtain a molecule to be screened for a desired activity. In embodiments, a diverged, codon-optimized nucleic acid sequence may be designed that encodes all or part of any polypeptide of interest.

A method of the invention may be used to design a synthetic nucleic acid sequence for a variety of reasons known to those of skill in the art; e.g., to increase expression, to adapt the nucleic acid sequence to be expressed in a new host cell or organism, and to introduce functional and/or non-functional mutations into an encoded polypeptide. Typically in embodiments where a reference amino acid sequence is a naturally-occurring gene product, or portion of a naturally-occurring gene product (e.g., an isolated protein domain), a naturally-occurring nucleic acid sequence encoding the reference amino acid sequence may be obtained, for example, by searching genome databases or cloning from a source genome. In many cases, homologues or orthologs of such nucleic acid sequences may also be found in the genomes of other organisms. In embodiments, diverged, codon-optimized nucleic acid sequences encoding all or part of a polypeptide of interest may be designed or derived from a sequence that encodes any reference polypeptide. In particular embodiments, the reference polypeptide and the polypeptide of interest comprise at least one amino acid repeat region(s).

In some embodiments, disclosed methods involve optimization of the nucleotide sequence of a synthetic nucleic acid molecule, such that the primary structure of an encoded polypeptide is unchanged. The structure of an encoded polypeptide is determined, to the greatest extent, by the amino acid sequence of the polypeptide. Thus, a desired structure for an encoded polypeptide places limitations on its nucleotide coding sequence that are determined by the degeneracy of the genetic code and standard codon usage. In certain embodiments of the invention, a synthetic nucleic acid molecule may be designed in silico such that the nucleic acid molecule comprises a specific diverged and codon-optimized sequence selected from the codon space that encodes all or part of a polypeptide of interest (e.g., an amino acid repeat region). Incorporation of the specific sequence that is selected may avoid certain problems associated with nucleotide sequences that encode polypeptides comprising amino acid repeat domains, and may achieve one or more desired properties (e.g., enhanced expression) when compared to sequences that are merely codon-optimized, for example, by reference to the codon usage bias of an expression host organism.

In some embodiments, nucleic acid sequence(s) that encode an amino acid repeat region of the polypeptide of interest may then each be extracted as a separate sequence from a nucleic acid sequence that encodes the entire protein of interest. The extracted sequences may be used to design a set of codon-optimized nucleotide sequences; for example, a set of nucleotide sequences that each encode an amino acid repeat region of the polypeptide of interest. The set of codon-optimized nucleotide sequences may then be used to design a diverged, codon-optimized nucleotide sequence. A variety of factors may be considered when a codon-optimized nucleotide sequence is designed. These factors may include the codon usage bias of an expression host organism.

A variety of methods are available to those skilled in the art for optimizing the coding sequence of a nucleic acid molecule (e.g., a nucleotide sequence encoding an amino acid repeat region of a peptide of interest) according to predetermined parameters. For example, the skilled artisan may optimize a coding sequence by inspection, e.g., to better conform to the codon usage bias of an expression host organism. More commonly, a computer-implemented software program may be used to optimize a coding sequence. Such software programs may comprise one or more algorithms that optimize factors selected from the group comprising: factors that may affect the expression of an encoded polypeptide of interest, factors that may affect the rate of translation initiation of a transcript, and factors that may affect the rate of translational elongation of the encoded polypeptide or its precursor. Particular examples of such software programs include, without limitation, OPTGENE™ (*Ocimum* Biosolutions), Accelrys GCG™ (Accelrys Software, Inc.), OPTIMIZER™ (available for public use on the world-wide web at genomes.urv.es/OPTIMIZER), and OPTIMUMGENE™ (GenScript).

In some embodiments, extracted sequences that each encode an amino acid repeat region of a polypeptide of interest may be codon-optimized by first deducing the amino acid sequence encoded by the extracted sequence (e.g., in silico translation). In further embodiments, the amino acid sequence of an amino acid repeat region may be used directly to obtain a codon-optimized nucleic acid sequence. In particular embodiments, the amino acid sequence of each amino acid repeat region (whether deduced from a nucleic acid sequence or provided directly) may be used to deduce a codon-optimized nucleic acid sequence encoding the amino acid repeat region (e.g., in silico reverse-translation), for example, by using a computer-implemented software program that is capable of optimizing a coding sequence according to predetermined parameters. In specific examples, a codon-optimized nucleic acid sequence may be deduced using the standard genetic code and an appropriate codon usage bias table for an expression host organism. It may be desirable in some embodiments to deduce multiple codon-optimized nucleic acid sequences encoding each amino acid repeat region. Thus, in particular examples, a single amino acid repeat region may be used to deduce a set of 1, 2, 3, 4, 5, 6, 7, 8, 9, 10, 11, 12, 13, 14, 15, 16, 17, 18, 19, 20, or more codon-optimized nucleic acid sequences encoding the amino acid repeat region. In some embodiments, deduced codon-optimized nucleic acid sequences encoding the amino acid repeat regions may be exported into text files by a computer-implemented software program, or otherwise recorded for the practitioner. For example, a computer-implemented software program may export into a corresponding number of text files for an entire set of deduced codon-optimized nucleic acid sequences encoding a single amino acid repeat region.

In some embodiments, the deduced codon-optimized nucleic acid sequences encoding an amino acid repeat region may be aligned by sequence homology. In particular examples, each sequence in every set of deduced codon-optimized nucleic acid sequences that correspond to all of the similar amino acid repeat region of a polypeptide of interest are all aligned to each other. Thus, a polypeptide that has 10 regions that are identified as similar repeats, for each of which 10 codon-optimized nucleic acid sequences are deduced, may be represented at this stage of a design process by an alignment of 100 nucleic acid sequences. In particular examples, the deduced codon-optimized nucleic acid sequences correspond to segments of protein coding regions, and the alignments may be performed with no "gaps" allowed.

In some embodiments, deduced codon-optimized nucleic acid sequences may be aligned using a computer-implemented software program (e.g., CLUSTALW™, Mega 3.1; available at www.megasoftware.net/). During or after alignment of the deduced sequences, an algorithm (e.g., the CLUSTAL™ algorithm) may assemble a neighbor-joining tree by methods known to those of skill in the art.

In particular embodiments, a neighbor-joining tree may be used to select a specific diverged, codon-optimized nucleic acid sequence for an amino acid repeat region in a polypeptide of interest. In some embodiments, the specific diverged, codon-optimized nucleic acid sequence may be selected from the set of deduced codon-optimized nucleic acid sequence that corresponds to the particular amino acid repeat region. In other embodiments, a neighbor-joining tree may be used to select a specific diverged, codon-optimized nucleic acid sequence for each amino acid repeat region in a polypeptide of interest. In particular examples, one of the set of deduced codon-optimized nucleic acid sequences that corresponds to a particular amino acid repeat region is selected from a section of the neighbor-joining tree that is most deeply branched, and the selected sequence is a diverged, codon-optimized nucleic acid sequence.

According to the foregoing, a method of the invention may be used to provide a single diverged, codon-optimized nucleic acid sequence encoding an amino acid repeat region of a polypeptide of interest. In particular examples, a method may be used to provide a set of single diverged, codon-optimized nucleic acid sequences, each of which encodes a different amino acid repeat region of a polypeptide of interest. For example, a set of single diverged, codon-optimized nucleic acid sequences may be provided, such that each and every amino acid repeat region in a polypeptide of interest is represented by a single diverged, codon-optimized nucleic acid sequence that encodes the same.

In some embodiments, a selected diverged, codon-optimized nucleic acid sequence encoding an amino acid repeat domain may be incorporated into an optimized nucleic acid sequence encoding an entire polypeptide of interest, such that the selected diverged, codon-optimized nucleic acid sequence is incorporated at the proper position for the particular repeat in the optimized nucleic acid sequence encoding the entire polypeptide of interest, while the correct reading frame for the polypeptide of interest is maintained. For example, all members of a set of single diverged, codon-optimized nucleic acid sequences, each of which encodes a different amino acid repeat region of a polypeptide of interest, may be incorporated into an optimized nucleic acid sequence encoding the entire polypeptide of interest, such that all members of the set are incorporated at their proper positions for the particular repeat in the entire sequence of the polypeptide of interest. In particular examples, all diverged, single codon-optimized nucleic acid sequences in a set that represents each and every amino acid repeat of a polypeptide of interest may be incorporated into an optimized nucleic acid sequence encoding the entire polypeptide of interest at their proper positions for the particular repeat in the sequence. Thus, some embodiments of the invention may be used to produce synthetic nucleic acid sequences encoding a polypeptide of interest, wherein every amino acid repeat region of the polypeptide is encoded by a diverged, codon-optimized nucleic acid sequence.

In many embodiments, it may be desirable for the entire nucleic acid sequence encoding a polypeptide to be optimized. Additionally, non-coding regions of a nucleic acid molecule comprising a sequence encoding a polypeptide of interest may be optimized. Thus, the invention also includes, in some embodiments, a synthetic nucleic acid molecule comprising an optimized sequence encoding a polypeptide of interest, wherein the optimized sequence comprises diverged, codon-optimized nucleic acid sequences encoding amino acid repeat regions, as set forth previously. The optimization of a nucleic acid sequence may include steps to improve the ability of the host to produce a foreign protein, as well as steps to assist a researcher in efficiently designing and assembling an expression construct. Optimization strategies may include, for example, the modification of translation initiation regions, alteration of mRNA structural elements, and the use of different codon biases.

Any method available to those skilled in the art may be utilized to optimize a nucleic acid sequence (e.g., a nucleotide sequence encoding an amino acid repeat region of a peptide of interest) according to predetermined parameters. For example, software programs such as, without limitation, OptGene™ (*Ocimum* Biosolutions), Accelrys GCG™ (Accelrys Software, Inc.), OPTIMIZER™ (available for public use on the world-wide web at genomes.urv.es/OPTI-MIZER), and OptimumGene™ (GenScript), may be utilized. Factors that may be considered during the optimization of a nucleotide sequence (e.g., a nucleotide sequence encoding a polypeptide of interest) may include, without limitation: factors that may affect the expression of an encoded polypeptide of interest; factors that may affect the rate of translation initiation of a transcript; and factors that may affect the rate of translational elongation of the encoded polypeptide or its precursor. The selection of which of these factors to be considered during the design of a set of codon-optimized sequences is within the discretion of the skilled practitioner.

Factors that may affect the expression of a polypeptide of interest that is encoded by a nucleic acid sequence may be influenced by the particular codons chosen to encode the amino acids of the polypeptide. Factors affecting the rate of production of mRNA from the template nucleic acid sequence may include: the RNA polymerase type used for transcription; the RNA polymerase level present in the expression system; and the transcription promoter sequence used. The mRNA levels may also be affected by the mRNA degradation rate, which in turn may be influenced by mRNA destabilizing motifs; RNAse recognition sequences; mRNA secondary structure; and polyA addition signals. The mRNA levels may also be affected by mRNA structures at the translational initiation site, at the ribosome binding site, at the start codon, and/or around the initial 10-50 codons of the coding sequence (or elsewhere within, or following, the open reading frame); transcriptional termination motifs present before or within the open reading frame; and signals within the transcribed sequence such as those that direct, alter, or modify mRNA splicing and/or nuclear export. A particular example of a factor affecting the rate of mRNA production from a template sequence is nucleotide repeat-induced polymerase slippage. Nucleotide repeat-induced polymerase slippage involves nucleotide sequence repeats that have been shown to cause slippage or stuttering of DNA polymerase which can result in frameshift mutations. Such nucleotide repeats can also cause slippage of RNA polymerase. For example, in an organism with a high G+C content bias, there can be a higher degree of G or C nucleotide repeats. Therefore, one method of reducing the possibility of inducing RNA polymerase slippage includes altering extended repeats of G or C nucleotides.

Factors that may affect the rate of translational initiation for a particular transcript include: the sequence of the ribosome binding site; sequences upstream of the ribosome binding site; sequences around the start codon (e.g., Kozak consensus sequences); the presence, relative location, and sequence of internal ribosome entry sites; the sequence and distance between the ribosome entry site (or the ribosome binding site or the 5' end of the mRNA) and the start codon; the mRNA structures at the translational initiation site; the mRNA structures at the ribosome binding site; the mRNA structures at the start codon; the mRNA structures around the initial 10-50 codons of the coding sequence; the sequence of the initial 10-20 codons; the GC bias of the initial 10-20 codons; the codon used at the codon adjacent to the start codon; the sequence of the start codon (AUG, UUG, or GUG); the ribosome concentration; the growth conditions before induction of expression; the growth conditions during expression; the temperature prior to induction of expression; and the temperature during expression.

Specific examples of factors that may affect the rate of translational initiation for a particular transcript include alternate translational initiation and interfering mRNA secondary structures. Alternate translational initiation may occur in a synthetic polynucleotide sequence that inadvertently contains one or more motifs capable of functioning as a ribosome binding site (RBS). These sites can result in initiating translation of a truncated protein from a gene-internal site. One method of reducing the possibility of producing a truncated protein, which can be difficult to remove during purification, includes modifying putative internal RBS sequences from an optimized polynucleotide sequence. Interfering secondary structures may sequester the RBS sequence or initiation codon, and have been correlated to a reduction in protein expression. Stem-loop structures can also be involved in transcriptional pausing and attenuation. An optimized polynucleotide sequence may thus contain minimal secondary structures in the RBS and gene coding regions of the nucleotide sequence to allow for improved transcription and translation.

Factors that may affect the rate of translational elongation include the level of charged tRNAs (Elf et al. (2003) Science 300:1718-22), which depends upon tRNA concentrations, tRNA charging rates, and amino acid availability. For example, a translational pause induced by a rare (or non-preferred) codon according to the host organism's codon usage bias may reduce the rate of heterologous protein expression. A rare codon-induced translational pause includes the presence of codons in the polynucleotide of interest that are rarely used in the host organism and may have a negative effect on protein translation due to their scarcity in the available tRNA pool. These factors also include the rate of ribosomal tRNA selection (decoding rate), which depends upon: the strength of the codon-anticodon interaction; the preceding codon (P-site codon); the wobble base of the preceding codon; and the wobble base of the codon being read. Factors that may affect ribosomal fidelity include those that influence ribosomal frameshifts, such as homopolymer stretches, G/C islands, A/T islands, and homopolymer stretches near pause sites. Furthermore, some polypeptides may be hindered in the ribosomal exit channel, which depends in part upon the sequence of the initial 10-20 amino acids of the polypeptide. In view of the foregoing, one method of improving optimal translation in a host organism includes performing codon optimization which can result in rare host codons being modified in a synthetic nucleic acid sequence.

Another class of nucleic acid sequence element that may affect (albeit indirectly) heterologous protein expression includes restriction sites. Thus, optimization of a nucleic acid sequence may include modification of restriction sites that could, for example, interfere with subsequent sub-cloning of transcription units into host expression vectors.

All or a portion of a nucleic acid sequence may be optimized. In some examples, a desired modulation of expression may be achieved by optimizing essentially an entire gene. In other examples, a desired modulation may be achieved by optimizing part, but not all, of a gene. Furthermore, the codon usage of any coding sequence may be adjusted to achieve a desired property, for example, high levels of expression in a specific expression host cell. The starting point for such an optimization may be a coding sequence that consists only of commonly-used or preferred codons, according to the codon usage bias of the expression host, or a coding sequence which contains a mixture of common and non-common codons. Optimizing a nucleic acid sequence can negatively or positively affect gene expression or protein production. For example, replacing a rare or non-preferred codon with a more common codon may affect the half life of an mRNA molecule transcribed from the sequence comprising the replaced codon, or alter its structure by introducing a secondary structure that interferes with its translation. It may therefore be necessary, in certain instances, to further alter an optimized sequence.

Within some embodiments, a synthetic nucleic acid sequence comprising diverged, codon-optimized nucleic acid sequences encoding amino acid repeat regions may comprise more than one optimized sequence. For example, such a sequence may encode a fusion polypeptide that comprises multiple polypeptides as described herein, or that comprises at least one polypeptide as described herein and an unrelated sequence. Fusion polypeptides may be prepared using standard techniques, including chemical conjugation, so as to permit translation into a single fusion polypeptide that retains at least one biological activity of both component polypeptides. A peptide linker sequence may be employed to separate polypeptide components of a fusion polypeptide by a distance sufficient to ensure that each polypeptide folds into appropriate secondary and tertiary structures. Such a peptide linker sequence may be incorporated into the fusion polypeptide using standard techniques well known in the art.

Synthetic nucleic acid sequences comprising diverged, codon-optimized nucleic acid sequences encoding amino acid repeat regions may be expressed for use in a variety of applications, for example, to produce a recombinant polypeptide; to develop a new expression system; to compare expression properties to those of other nucleic acid sequences; and for diagnostic applications.

V. Expression of a Diverged, Codon-Optimized Nucleic Acid Sequence

This disclosure provides methods of producing a polypeptide of interest comprising amino acid repeats in the cytoplasm and/or periplasm of a cell. Some embodiments utilize a synthetic nucleic acid sequence optimized for heterologous expression in a host organism (e.g., a bacterial host organism). An optimized synthetic nucleic acid sequence encoding a polypeptide comprising amino acid repeat regions may comprise diverged, codon-optimized nucleic acid sequences encoding amino acid repeat regions. In particular embodiments, such an optimized synthetic nucleic acid sequence may be ligated into an expression vector, and the expression vector comprising the optimized nucleic acid sequence may be introduced into an expression host cell (e.g., by transformation), wherein a polypeptide is expressed from the optimized synthetic nucleic acid sequence.

Nucleic acid molecules comprising synthetic nucleic acid sequences encoding a polypeptide of interest may be produced by methods known to those of skill in the art. For example, in some embodiments, relatively short segments of a desired nucleic acid sequence may be reliably synthesized, followed by concatenation. Advances in the field of DNA synthesis have allowed the reliable synthesis of longer nucleic acid sequences, as well as relatively shorter, nucleic acid segments. Synthetic techniques allow reasonably accurate oligonucleotide synthesis of 300 bases or more. Thus, in some embodiments, longer sequences may be synthesized, such that concatenation may not be required. However, synthetic chemically-produced oligonucleotides are typically between 20 and 100 bp in length. In some embodiments, a synthetic gene or gene fragment may be prepared using PCR in a step-wise fashion by the annealing and extension of synthetic alternating and overlapping sense and antisense oligomers (for example, 90-110 bp in length) designed to encode the final desired sequence.

Oligonucleotide production may include oligo-synthesis carried out by the phosporamidite protocol as a solid phase synthesis. Briefly, a first nucleotide with its 5'-OH functional group protected by a 5'-O-dimethoxytrityl (DMT) group may be coupled to polystyrene beads as a solid phase. Next, the DMT-group may be removed by acid treatment, generating a free 5'-OH group. Then, the phosporamidite of choice may be added, converted to a reactive intermediate in weakly acidic conditions, and coupled to the free 5'-OH group to produce a novel phosphite linkage. These reactions may take place in tetrahydrofuran or dimethyl sulfoxide. As the 5'-OH of the added nucleotide remains protected, only one nucleotide is added to the growing chain. The 5'-OH groups that do not react may be capped so that they cannot continue to take part in the synthesis process and generate oligonucleotides with deletions. This may be achieved by acetylation after treatment with acetic acid and 1-methyl-imidazole. Finally, water and iodine may be added to oxidize the phosphite linkage to a phosphodiester linkage. In between steps, the production system may be conditioned by washing with a suitable solvent. After repeating this sequence of steps as required, the oligonucleotide may finally be cleaved from the column, and treated with ammonium hydroxide at high temperature to remove all remaining protecting groups. This process may be made more efficient by use of a photolithography approach, for example, as provided by NIMBLEGEN™ (Febit, Germany).

After short oligonucleotides have been produced by solid state synthesis, the oligonucleotides may be assembled into larger DNA fragments, for example, to a size of about 500 bp. This is typically achieved by one of a variety of enzyme-assisted methods. For example, short overlapping oligonucleotide pairs may be used to generate longer dsDNA molecules via a Klenow extension reaction. The corresponding oligonucleotides may be mixed, hybridized, and then converted to larger assemblies by PCA. In a PCA reaction, all oligonucleotides that together represent the targeted double-stranded DNA fragment are present. By repeated melting and re-hybridization, the oligonucleotides are step-by-step extended into longer sections until a certain population reaches the desired length. Note that this reaction is carried out without terminal oligonucleotide in excess, so it is not an amplification reaction. Rather, every full-length fragment consists of oligonucleotides and their extensions, thereby reducing the chance of introducing errors by polymerase action. An alternative methodology to PCA is polymerase assembly multiplexing (PAM), wherein terminal primers are added to a pool of oligonucleotides such that only a specific subset of the oligonucleotides is amplified. In a second round of PAM reactions, multiple oligonucleotides can be recombined into a single DNA molecule by using a novel set of primers.

Large oligonucleotides (for example, oligonucleotides produced by PCA, PMA, etc.) may be assembled into still larger DNA molecules, for example, by restriction digestion and ligation.

A variety of expression systems can be used for expression of a polypeptide from an optimized nucleic acid sequence of the invention. In some embodiments, an expression system may be, for example and without limitation: a bacterial expression system, such as *Escherichia coli*, *Salmonella* spp., *Bacillus* spp., *Streptomyces* spp., *Pseudomonas* spp. (e.g., *P. fluorescens*), *Ralstonia eutropha*, *Chlamydomonas* spp.; yeast expression systems including *Saccharomyces*, *Pichia*, *Klebsiella*, and *Candida* species, *S. cerevisiae*, *P. pastoris*, *P. methanolica*, and *K. lactis*; fungal expression systems including *Cryptosporidium* and *Trichoderma* spp.; filamentous fungal protein production systems; protozoan expression systems including *Plasmodium falciparum* and *Leishmania*; model organisms including *Caenorhabditis elegans*, *Drosophila melanogaster*, and *Xenopus laevis*; plants including soybean, bushbean, maize, cotton, tobacco, and *Arabidopsis*; mammalian tissue culture expression systems including COS cells, Chinese Hamster Ovary cells, and fibroblasts such as 3T3 cells; cell lines infected with adenovirus; insect cell lines such as those derived from *Spodoptera* spp. for growing baculovirus; in vitro expression systems prepared from extracts of living cells such as *E. coli* extracts, wheat germ extracts, rabbit reticulocyte lysates; and in vitro expression systems prepared by assembly of purified individual components.

In embodiments wherein a polypeptide of interest comprising amino acid repeat regions is to be expressed in a prokaryotic cell or expression system, an optimized nucleic acid sequence encoding the polypeptide of interest may first be cloned into a prokaryotic vector by linearizing a vector having an origin of replication and convenient restriction sites, which may involve a polylinker, for insertion of the nucleic acid sequence. The vector may also have a marker gene for selection, which may impart antibiotic resistance or afford another distinguishing characteristic (e.g., chromophore or fluorophore formation). There are a wide variety of antibiotic reagents (e.g., tetracycline, chloramphenicol, actinomycin, neomycin, ampicillin, hygromycin, heavy metals, etc.) that may be utilized for marker-assisted selection. Other markers include β-galactosidase, which converts the substrate X-gal to provide a blue color when it is expressed. Numerous vectors are commercially available for cloning in bacteria, and these vectors are well-known to those of skill in the art. In some embodiments, a prokaryotic vector comprising one or more optimized synthetic nucleic acid sequence(s) comprising diverged, codon-optimized nucleic acid sequences encoding amino acid repeat regions may then be introduced into an appropriate cloning host by any convenient means, including without limitation; calcium phosphate precipitated DNA, fusion, transfection, and conjugation. The cells may then be grown in an appropriate selective nutrient medium. Surviving cells may be harvested, lysed, and the plasmid isolated.

A prokaryotic expression vector may be characterized by having an origin of replication which is functional in an appropriate expression host, usually for episomal maintenance, and a marker for selection. For unintegrated vectors or constructs, the origin of replication will usually provide for multicopies, for example, at least about 5 copies on the average. The expression vector typically will also have a promoter which is functional in the expression host. A large number of promoters are available and particular promoters may, for example, provide for a high level of either inducible or constitutive transcription. Illustrative promoters that may be useful in some embodiments include, without limitation: β-lactamase; α-galactosidase; $\lambda P_L$ or $\lambda P_R$ promoters; trpE promoter; trp-lac promoter; T7 promoter (particularly genes 9 and 10); and $cI^{ts}$.

A nucleic acid molecule comprising an optimized sequence including diverged, codon-optimized nucleic acid sequences encoding amino acid repeat regions may be combined with a linearized vector by hybridization, for example, ligation. Where the optimized sequence does not have an initiation codon, such a codon can be added. In some embodiments, a nucleic acid molecule may be inserted into a coding sequence present in the vector (in an appropriate reading frame), under the transcriptional control of a promoter. A signal sequence may be included at the 5' terminus of a coding sequence to allow for secretion of the polypeptide product into the periplasmic space. Generally, the product will be produced intracellularly.

Instead of a vector, DNA constructs may be employed for transformation of an expression host, where the construct may be integrated into the genome of the expression host. The construct may lack an origin of replication that provides for episomal maintenance. A construct may comprise at least transcriptional and translational initiation and termination regions, and an optimized sequence encoding a polypeptide comprising amino acid repeat regions may be positioned between the initiation and termination regions and under their regulatory control. A construct may further comprise a selection marker and/or other functional sequences, for example and without limitation, homologous sequences for integration into the host genome; sequences that hybridize to PCR primers; and restriction sites.

In some embodiments, an expression host may be a plant cell, such as, for example, a plant cell in a plant tissue culture or whole plant. Embodiments of the invention may include plant cells from any tissue or wherever they are found, including but not limited to, in embryos, meristematic cells, callus, pollen, leaves, anthers, roots, root tips, flowers, seeds, pods, stems, and tissue culture. A synthetic optimized nucleic acid sequence of the invention may be incorporated into an appropriate vector, and introduced into a plant cell by any method known to those of skill in the art. For example, a nucleic acid molecule may be introduced into a plant cell by methods including, without limitation, transfection with viral vectors, transformation with plasmid vectors, electroporation (Fromm et al. (1986) Nature 319:791-3), lipofection (Feigner et al. (1987) Proc. Natl. Acad. Sci. USA 84:7413-7), microinjection (Mueller et al. (1978) Cell 15:579-85), *Agrobacterium*-mediated transfer (Fraley et al.

(1983) Proc. Natl. Acad. Sci. USA 80:4803-7), direct DNA uptake, and microprojectile bombardment (Klein et al. (1987) Nature 327:70).

In some embodiments, a nucleic acid molecule may be introduced into a particular part of a plant cell (e.g., via nanoparticle bombardment). Examples of particular parts of plant cells into which a nucleic acid molecule may be introduced include, but are not limited to: cytosol, nucleus, tonoplasts, plastids, etioplasts, chromoplasts, leucoplasts, elaioplasts, proteinoplasts, amyloplasts, chloroplasts, and the lumen of a double membrane.

Cell transformation (including plant cell transformation) may involve the construction of an expression vector which will function in a particular cell. Such a vector may comprise DNA that includes a gene under control of, or operatively linked to, a regulatory element (for example, a promoter). The expression vector may contain one or more such operably-linked gene/regulatory element combinations. The vector(s) may be in the form of a plasmid and can be used alone or in combination with other plasmids to provide transformed cells using transformation methods as described herein to incorporate transgene(s) into the genetic material of a plant cell.

Plant cell expression vectors may include at least one genetic marker, operably linked to a regulatory element (a promoter, for example) that allows transformed cells containing the marker to be either recovered by negative selection (i.e., inhibiting growth of cells that do not contain the selectable marker gene) or by positive selection (i.e., screening for the product encoded by the genetic marker). Many selectable marker genes suitable for plant transformation are well known in the transformation arts and include, for example, genes that code for enzymes that metabolically detoxify a selective chemical agent which may be an antibiotic or an herbicide, or genes that encode an altered target which may be insensitive to the inhibitor. A few positive selection methods are also known in the art. In some embodiments, selectable marker genes suitable for plant transformation may include: the neomycin phosphotransferase II (nptII) gene under the control of plant regulatory signals, which confers resistance to kanamycin (See, e.g., Fraley et al. (1983) Proc. Natl. Acad. Sci. U.S.A. 80:4803); the hygromycin phosphotransferase gene, which confers resistance to the antibiotic, hygromycin (See, e.g., Van den Elzen et al. (1985) Plant Mol. Biol., 5:299); marker genes of bacterial origin that confer resistance to antibiotics, including gentamycin acetyl transferase, streptomycin phosphotransferase, aminoglycoside-3'-adenyl transferase, and the bleomycin resistance determinant (See Hayford et al. (1988) Plant Physiol. 86:1216; Jones et al. (1987) Mol. Gen. Genet. 210:86; Svab et al. (1990) Plant Mol. Biol. 14:197; and Hille et al. (1986) Plant Mol. Biol. 7:171); marker genes that confer resistance to herbicides such as glyphosate, glufosinate or bromoxynil (See Comai et al. (1985) Nature 317: 741-744; Gordon-Kamm et al. (1990) Plant Cell 2:603-618; and Stalker et al. (1988) Science 242:419-423); and marker genes not of bacterial origin including, for example, mouse dihydrofolate reductase, plant 5-enolpyruvylshikimate-3-phosphate synthase, and plant acetolactate synthase (See Eichholtz et al. (1987) Somatic Cell Mol. Genet. 13:67; Shah et al. (1986) Science 233:478; and Charest et al. (1990) Plant Cell Rep. 8:643).

Another class of marker genes suitable for plant transformation requires screening of presumptively transformed plant cells rather than direct genetic selection of transformed cells for resistance to a toxic substance, such as an antibiotic. These genes may be particularly useful to quantify or visualize the spatial pattern of expression of a gene in specific tissues, and they are frequently referred to as reporter genes because they can be fused to a gene or gene regulatory sequence for the investigation of gene expression. Commonly used genes for screening transformed cells include β-glucuronidase (GUS), β-galactosidase, luciferase, and chloramphenicol acetyltransferase. See Jefferson (1987) Plant Mol. Biol. Rep. 5:387; Teeri et al. (1989) EMBO J. 8:343; Koncz et al. (1987) Proc. Natl. Acad. Sci. U.S.A. 84:131; and DeBlock et al. (1984) EMBO J. 3:1681. Methods are available for visualizing GUS activity in vivo that do not require destruction of plant tissue. Molecular Probes publication 2908 (1993) IMAGENE GREEN™, pp. 1-4; and Naleway et al. (1991) J. Cell Biol. 115:151. Genes encoding fluorescent proteins (e.g., GFP, EGFP, EBFP, ECFP, and YFP) have also been utilized as markers for gene expression in prokaryotic and eukaryotic cells. See Chalfie et al. (1994) Science 263:802. Thus, fluorescent proteins and mutations of fluorescent proteins may be used as screenable markers.

Expression of a coding sequence included in a plant expression vector may be driven by a nucleotide sequence comprising a regulatory element, for example, a promoter. Several types of promoters useful in plant cells are now well known in the transformation arts, as are other regulatory elements that can be used alone or in combination with such promoters.

The term "promoter" refers to a region of DNA that may be upstream from the start of transcription and that may be involved in recognition and binding of RNA polymerase and other proteins to initiate transcription. A "plant promoter" may be a promoter capable of initiating transcription in plant cells. Examples of promoters under developmental control include promoters that preferentially initiate transcription in certain tissues, for example, in leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily drives expression in certain cell types in one or more organs, for example, vascular cells in roots or leaves. An "inducible" promoter is a promoter which may be under environmental control. Examples of environmental conditions that may affect transcription by inducible promoters include, without limitation, anaerobic conditions or the presence of light. Tissue-specific, tissue-preferred, cell type-specific, and inducible promoters constitute the class of "non-constitutive" promoters. A "constitutive" promoter is a promoter which may be active under most environmental conditions and most tissues and cell types.

An inducible promoter may be operably linked to an optimized nucleotide sequence of the invention for expression in a cell. Optionally, an inducible promoter may be operably linked to a nucleotide sequence encoding a signal sequence, which may be operably linked to a nucleotide sequence of the invention for expression in a cell. The rate of transcription of a nucleotide sequence operably linked to an inducible promoter may increase in response to an inducing agent. Any inducible promoter may be used in the instant invention. See Ward et al. (1993) Plant Mol. Biol. 22:361-366. Exemplary inducible promoters include, but are not limited to: those from the ACEI system that responds to copper (Mett et al. (1993) Proc. Natl. Acad. Sci. U.S.A. 90:4567-71); In2 gene from maize that responds to benzenesulfonamide herbicide safeners (Hershey et al. (1991) Mol. Gen Genetics 227:229-37; and Gatz et al. (1994) Mol. Gen. Genetics 243:32-8); and Tet repressor from Tn10 (Gatz et al. (1991) Mol. Gen. Genetics 227:229-37). A particularly useful inducible promoter may be a promoter that responds to an inducing agent to which plants do not normally respond. An exemplary inducible promoter may be the inducible promoter from a steroid hormone gene, the transcriptional activity of which may be induced by a glucocorticosteroid hormone. Schena et al. (1991) Proc. Natl. Acad. Sci. U.S.A. 88:10421-5.

Alternatively, a constitutive promoter may be operably linked to an optimized nucleotide sequence of the invention for expression in a cell, or the constitutive promoter may be operably linked to a nucleotide sequence encoding a signal sequence which may be operably linked to a nucleotide sequence of the invention for expression in a cell. Different constitutive promoters may be utilized in the instant invention. Exemplary constitutive promoters include, but are not limited to: promoters from plant viruses, such as the 35S promoter from CaMV (Odell et al. (1985) Nature 313:810-2); promoters from rice actin genes (McElroy et al. (1990) Plant Cell 2:163-71); ubiquitin (Christensen et al. (1989) Plant Mol. Biol. 12:619-32; and Christensen et al. (1992) Plant Mol. Biol. 18:675-89); pEMU (Last et al. (1991) Theor. Appl. Genet. 81:581-8); MAS (Velten et al. (1984) EMBO J. 3:2723-30); and maize H3 histone (Lepetit et al. (1992) Mol. Gen. Genetics 231:276-85; and Atanassova et al. (1992) Plant Journal 2(3):291-300). The ALS promoter, Xba1/NcoI fragment 5' to the *Brassica napus* ALS3 structural gene (or a nucleotide sequence similarity to said Xba1/NcoI fragment), represents a particularly useful constitutive promoter. See International PCT Publication No. WO 96/30530.

A tissue-specific promoter may alternatively be operably linked to an optimized nucleotide sequence of the invention for expression in a cell. Optionally, the tissue-specific promoter may be operably linked to a nucleotide sequence encoding a signal sequence which may be operably linked to an optimized nucleotide sequence of the invention for expression in a cell. Plants transformed with an optimized nucleotide sequence of the invention operably linked to a tissue-specific promoter may produce a protein product of the nucleotide sequence exclusively, or preferentially, in a specific tissue. Any tissue-specific or tissue-preferred promoter can be utilized in the instant invention. Exemplary tissue-specific or tissue-preferred promoters include, but are not limited to: a seed preferred promoter, such as that from the phaseolin gene (Murai et al. (1983) Science 23:476-82; and Sengupta-Gopalan et al. (1985) Proc. Natl. Acad. Sci. U.S.A. 82:3320-4); a leaf-specific and light-induced promoter such as that from cab or rubisco (Simpson et al. (1985) EMBO J. 4(11):2723-9; and Timko et al. (1985) Nature 318:579-82); an anther-specific promoter such as that from LAT52 (Twell et al. (1989) Mol. Gen. Genetics 217:240-5); a pollen-specific promoter such as that from Zm13 (Guerrero et al. (1993) Mol. Gen. Genetics 244:161-168); and a microspore-preferred promoter such as that from apg (Twell et al. (1993) Sex. Plant Reprod. 6:217-224).

Transport of a polypeptide expressed from an optimized nucleotide sequence of the invention to a subcellular compartment, such as the chloroplast, vacuole, peroxisome, glyoxysome, cell wall, or mitochondrion, or for secretion into the apoplast, can be accomplished by means of operably linking a nucleotide sequence encoding a signal sequence to the 5' and/or 3' region of the sequence encoding the polypeptide. Targeting sequences at the 5' and/or 3' end of the structural gene may determine, during protein synthesis and processing, where the encoded protein may be ultimately compartmentalized. Alternatively, subcellular compartment targeting proteins may be directly linked to a nanoparticle to direct the nanoparticle coated with the molecule of interest to a desired subcellular compartment. Many signal sequences are known in the art. See, e.g., Becker et al. (1992) Plant Mol. Biol. 20:49; Close, P. S. (1993) Master's Thesis, Iowa State University; Knox et al. (1987) Plant Mol. Biol. 9:3-17; Lerner et al. (1989) Plant Physiol. 91:124-129; Fontes et al. (1991) Plant Cell 3:483-496; Matsuoka et al. (1991) Proc. Natl. Acad. Sci. U.S.A. 88:834; Gould et al. (1989) J. Cell. Biol. 108:1657; Creissen et al. (1991) Plant J. 2:129; Kalderon et al. (1984) Cell 39:499-509; and Steifel et al. (1990) Plant Cell 2:785-793.

In view of the foregoing, it will be understood that an expression host for use in embodiments of the invention may be a unicellular prokaryotic or eukaryotic organism, but may also be a multicellular organism. The expression host may, for example, be selected from a group comprising bacteria; algae; fungi (e.g., yeast); insect cells; plant cells (e.g., maize, soybean, and *Brassica napus*); animal cells; baculovirus; mammalian tissue culture; plants tissue culture; and whole plants (e.g., *B. napus*). In embodiments where the expression host is a multicellular organism (e.g., a plant), a vector or DNA construct may be introduced into one or more cells of the multicellular organism, and expressed therein. In some examples, a whole organism may be produced from one or more cells of the multicellular organism comprising an introduced vector or DNA construct. For example, methods of regenerating a whole plant from plant cells transformed with a nucleic acid molecule of interest, and subsequently selecting for a plant that has integrated the nucleic acid molecule into its genome, are known in the art.

The expression host cell comprising an introduced vector or DNA construct may be grown in an appropriate medium in culture (e.g., fermentation). After the cells have been grown to an appropriate density, the cells may be harvested, lysed, and the expression product may be isolated in accordance with its physical and chemical characteristics. In some embodiments, an expression product may be insoluble at moderate temperatures in an aqueous medium, and may be purified by detergent extraction at mildly elevated temperatures. See U.S. Pat. No. 5,235,041. As appropriate, the crude or purified expression product may then be used for its intended purpose.

Embodiments of the invention allow for the expression of any polypeptide of interest. In some examples, the polypeptide of interest may be itself desirable for an application (e.g., a polymer). In other examples, the polypeptide of interest may be expressed in the host to produce a further desirable polypeptide, small molecule, or other substance (e.g., an enzyme), or to introduce a desired phenotype in the host. In particular examples, a polypeptide of interest may be: a protein that is not normally found in cells of the expression host; an agronomic gene product; a polypeptide that confers resistance to pests or disease; a *Bacillus thuringiensis* protein; a lectin; a vitamin-binding protein (e.g., avidin); an enzyme inhibitor; an insect-specific hormone or pheromone; a peptide or neuropeptide that is specific to a particular organism; a venom; an enzyme responsible for a hyperaccumulation of a monoterpene, a sesquiterpene, a steroid, hydroxamic acid, a phenylpropanoid derivative or other non-protein molecule; an enzyme involved in the modification, including the post-translational modification, of a biologically active molecule (e.g., an enzyme involved in omega-3 fatty acid synthesis); a signal transduction molecule or molecule that stimulates signal transduction (e.g., calmodulin); a hydrophobic movement peptide; a membrane permease, transporter, or channel; a channel former or channel blocker; a viral-invasive protein or complex toxin derived therefrom; an antibody or immunotoxin (e.g., a virus-specific antibody); a developmental-arrestive protein; a polypeptide that confers resistance to an herbicide, fungicide, or other harmful small molecule; scaffolding proteins; and synthetic polypeptides that are designed to have a particular function (e.g., a function attributable to amino acid repeat regions, such as binding properties or physical characteristics). In some embodiments, a polypeptide of interest may be appropriated from nature. In other embodiments, a polypeptide of interest may be a polypeptide that is not normally found in nature.

In some embodiments, two or more different candidate sequences that were generated by sequence optimization using different parameters (e.g., sequences that differ in their codon usage) may be generated and tested to determine if they possess the desired property. Candidate sequences may be evaluated, for example, to search for the presence of regulatory elements, such as silencers or enhancers, or to search for the presence of regions of coding sequence which could be converted into such regulatory elements by an alteration in codon usage. Additional criteria may include enrichment or reduction for particular nucleotides (e.g., A, C, G or U, codon bias for a particular amino acid), or the presence or absence of particular mRNA secondary or tertiary structure. Adjustment to the candidate sequence for further expression may be made based on such criteria.

Promising candidate sequences may be constructed and evaluated experimentally. Multiple candidates may be evaluated independently of each other, or the process can be iterative, either by using the most promising candidate as a new starting point, or by combining regions of two or more candidates to produce a novel hybrid. Further rounds of modification and evaluation may be desirable.

VI. Genetically-Modified Organisms Comprising a Diverged, Codon-Optimized Nucleic Acid Sequence This disclosure also provides genetically-modified organisms comprising a diverged, codon-optimized nucleic acid sequence. In some embodiments, such an organism may include a synthetic optimized nucleic acid sequence encoding a polypeptide of interest comprising amino acid repeat regions. A synthetic optimized nucleic acid sequence encoding a polypeptide of interest comprising amino acid repeat regions may be operably linked to regulatory sequences (e.g., a promoter) appropriate to the organism, as previously set forth. In particular embodiments, the organism may express the polypeptide of interest. In certain embodiments, a polypeptide of interest may be expressed from an optimized nucleic acid sequence of the invention at a level which is at least 105%, 110%, 150%, 200%, 500%, 1,000%, 5,000% or even 10,000% of that expressed by a nucleic acid sequence encoding the same polypeptide that has not been optimized.

In some embodiments, a genetically-modified organism comprising a diverged, codon-optimized nucleic acid sequence is a genetically-modified plant, wherein at least some of the cells of the genetically-modified plant comprise one or more synthetic optimized nucleic acids of the invention. In one example of an embodiment, a plasmid comprising a nucleic acid sequence of the invention and a selectable marker are introduced into a plant cell, for example, by any of the methods previously enumerated herein. Stable transformants that have stably integrated the nucleic acid sequence and/or the selectable marker may be selected from such plant cells. In some embodiments, a plant cell comprising the nucleic acid sequence (for example, a stable transformant that has been selected) may be propagated to produce new plant cells comprising the nucleic acid sequence. Plant cells comprising a nucleic acid sequence of the invention may be a regenerable cell that may be used to regenerate a whole plant. Such plant cells and whole plants generated therefrom may express a polypeptide of interest comprising amino acid repeat regions that is encoded by the nucleic acid molecule.

In these and further embodiments, methods of creating regenerable plant cells comprising a synthetic optimized nucleic acid sequence of the invention (e.g., for use in tissue culture) may be provided. A tissue culture may be capable of regenerating plants having substantially the same genotype as the regenerable cells. The regenerable cells in such tissue cultures may be embryos, protoplasts, meristematic cells, callus, pollen, leaves, anthers, roots, root tips, flowers, seeds, pods or stems. Some embodiments of the invention provide plants regenerated from the tissue cultures of the invention.

Also provided by the invention are methods for generating stabilized plant lines comprising a synthetic optimized nucleic acid sequence of the invention, wherein cells of the stabilized plant lines may express a polypeptide of interest comprising amino acid repeat regions that are encoded by the nucleic acid sequence. Methods of generating stabilized plant lines are known to one of ordinary skill in the art, and may include techniques such as, but not limited to, selfing, backcrosses, hybrid production, and crosses to populations. All plants and plant cells comprising a synthetic optimized nucleic acid sequence of the invention are within the scope of this invention. Such plants and plant cells do not exist in nature, and they may exhibit advantageous expression properties of a polypeptide of interest, for example, when compared to a plant or plant cell comprising a nucleic acid sequence encoding the same amino acid repeat-containing polypeptide that has not been optimized according to the methods disclosed herein. Plant cells comprising a nucleic acid sequence of the invention may be used in crosses with other, different, plant cells to produce first generation ($F_1$) hybrid cells, seeds, and/or plants with superior or desirable characteristics.

In particular embodiments, a synthetic optimized nucleic acid sequence of the invention is utilized to produce genetically-modified *Brassica napus* plants. In further embodiments, genetically-modified plants produced using a synthetic optimized nucleic acid sequence of the invention may be, for example and without limitation: tobacco, carrot, maize, canola, rapeseed, cotton, palm, peanut, soybean, sugarcane, *Oryza* sp., *Arabidopsis* sp., and *Ricinus* sp.

Further embodiments of the invention provide for the heterologous expression of a polypeptide of interest comprising amino acid repeat regions from a synthetic optimized nucleic acid sequence in a bacterial host. Also included are synthetic optimized nucleic acid sequences encoding a recombinant protein comprising amino acid repeat regions that can be expressed using a heterologous bacteria-based expression system. Some examples include the heterologous expression of a polypeptide of interest comprising amino acid repeat regions from a synthetic optimized nucleic acid sequence in the cytoplasm of a bacterial host cell. An additional embodiment includes heterologous expression of a polypeptide of interest comprising amino acid repeat regions from a synthetic optimized nucleic acid sequence in the periplasm of a bacterial host cell.

In some embodiments, a bacterial host cell may be selected from an appropriate population of *E. coli* cells or *Pseudomonas* cells. In particular embodiments, the host cell may be any of the Proteobacteria of the order Pseudomonadales. A host cell may be any of the Proteobacteria of the family Pseudomonadaceae. In a particular embodiment, the host cell can be selected from one or more of the following: Gram-negative Proteobacteria Subgroup 1, 2, 3, 5, 7, 12, 15, 17, 18 or 19.

Particular examples include heterologous expression of such a polypeptide of interest in pseudomonads or bacteria closely related thereto. Pseudomonads and closely related bacteria, as used herein, is co-extensive with the group defined herein as "Gram(−) Proteobacteria Subgroup 1." "Gram(−) Proteobacteria Subgroup 1" is more specifically defined as the group of Proteobacteria belonging to the families and/or genera described as falling within that taxonomic "Part" named "Gram-Negative Aerobic Rods and Cocci" by R. E. Buchanan and N. E. Gibbons (eds.) (1974), Bergey's Manual of Determinative Bacteriology, pp. 217-289, 8th Ed., The Williams & Wilkins Co., Baltimore, Md., USA. A bacterial host cell may be selected from Gram-negative Proteobacteria Subgroup 18, which is defined as the group of all subspecies, varieties, strains, and other sub-special units of the species *Pseudomonas fluorescens*, including those belonging, e.g., to the following (with the ATCC or other deposit numbers of exemplary strain(s) shown in parenthesis): *P. fluorescens* biotype A, also called biovar 1 or biovar I (ATCC 13525); *P. fluorescens* biotype B, also called biovar 2 or biovar II (ATCC 17816); *P. fluorescens* biotype C, also called biovar 3 or biovar III (ATCC 17400); *P. fluorescens* biotype F, also called biovar 4 or biovar IV (ATCC 12983); *P. fluorescens* biotype G, also called biovar 5 or biovar V (ATCC 17518); *P. fluorescens* biovar VI; *P. fluorescens* Pf0-1; *P. fluorescens* Pf-5 (ATCC BAA-477); *P. fluorescens* SBW25; and *P. fluorescens* subsp. *cellulosa* (NCIMB 10462). A bacterial host cell may also be selected from Gram-negative Proteobacteria Subgroup 19, which is defined as the group of all strains of *P. fluorescens* biotype A, including *P. fluorescens* strain MB 101, and derivatives thereof.

A synthetic optimized nucleic acid sequence of the invention may be introduced into a bacterial host cell by any method known to those of skill in the art, for example, by transformation. Transformation of bacterial host cells with a nucleic acid sequence of the invention may be performed using any transformation methodology known in the art, and the bacterial host cells may be transformed as intact cells or as protoplasts (i.e., including cytoplasts). Transformation methodologies include poration methodologies (e.g., electroporation, protoplast fusion, bacterial conjugation, and divalent cation treatment, such as calcium chloride treatment or $CaCl_2/Mg^{2+}$ treatment), as well as other known methods in the art. See, e.g., Morrison (1977) J. Bacteriol. 132:349-51; Clark-Curtiss and Curtiss, (1983) Methods in Enzymology 101:347-62; Sambrook et al. (1989) Molecular Cloning, A Laboratory Manual, 2nd ed.; Kriegler (1990) Gene Transfer and Expression: A Laboratory Manual; and Ausubel et al. (eds.) (1994) Current Protocols in Molecular Biology.

The following examples are provided to illustrate certain particular features and/or embodiments. The examples should not be construed to limit the disclosure to the particular features or embodiments exemplified.

EXAMPLES

Example 1

Codon-Optimization of a Coding Sequence Containing Large Repeated DNA Sequences

To exemplify the optimization of a nucleic acid sequence encoding a polypeptide comprising amino acid repeat regions, a *Brassica napus*-optimized coding region was designed for the protein encoded by "ORFA" of *Schizochytrium* polyunsaturated fatty acid (PUFA) synthase.

The structure of the protein encoded by "ORFA" of *Schizochytrium* PUFA synthase is depicted in FIG. 1. The protein comprises 10 repeated "Pro-Ala" domains, ranging in size from 17 to 29 amino acids (SEQ ID NOs:1-10 and FIG. 2). Interspersed between the repeated Pro-Ala domains (see FIG. 1) are nine longer repeated sequence domains comprising 87 amino acids (SEQ ID NOs:11-19 and FIG. 3). The amino acid sequences of these repeats vary at only four positions and there are only two amino acid choices at each of the variant positions. CLUSTALW™ analyses of the amino acid sequences of the nine repeats (FIG. 3) generated a homology value of 100%, and an identity value of 95.4%. At the DNA level, the native *Shizochytrium* sequences encoding the nine repeats are 100% homologous and 89.7% identical, varying at only 27 positions in the 261 bases encoding each repeat (FIG. 4) 23 of the 27 changes are "silent" differences, in which synonymous codons for the same amino acid are interchanged. Standard gene design processes cannot easily accommodate developing new codon biased DNA sequences for multiple repeats of this size, since one must continually balance all the codon choices in an individual repeat with the codon choices made at the same position in the other 8 repeats, to avoid generating highly related DNA sequences.

For each of the 87-residue repeats, there are more than $4.5 \times 10^{43}$ possible DNA sequences to encode the same amino acid sequence. This number was calculated as the product of the number of synonymous codons for each amino acid in the sequence (bottom line of the alignments in FIG. 3). Thus, there is a very large codon space available to generate identically-encoding DNA sequences. Multiple sequence designs for each individual repeat were generated (in silico) and subsequently all the sequence versions were compared in bulk to identify a set that represents highly diverged sequences encoding the repeats.

First, the native DNA sequences encoding each repeated amino acid domain were extracted as a separate sequence, as illustrated in FIG. 4. Then, the individual repeated DNA sequences were imported as separate sequences into the OPTGENE™ gene design program (*Ocimum* Biosolutions). Steps 3-5 were subsequently performed on each individual sequence separately.

Step 3: An individual DNA sequence was translated using the standard genetic code.

Figure 5:
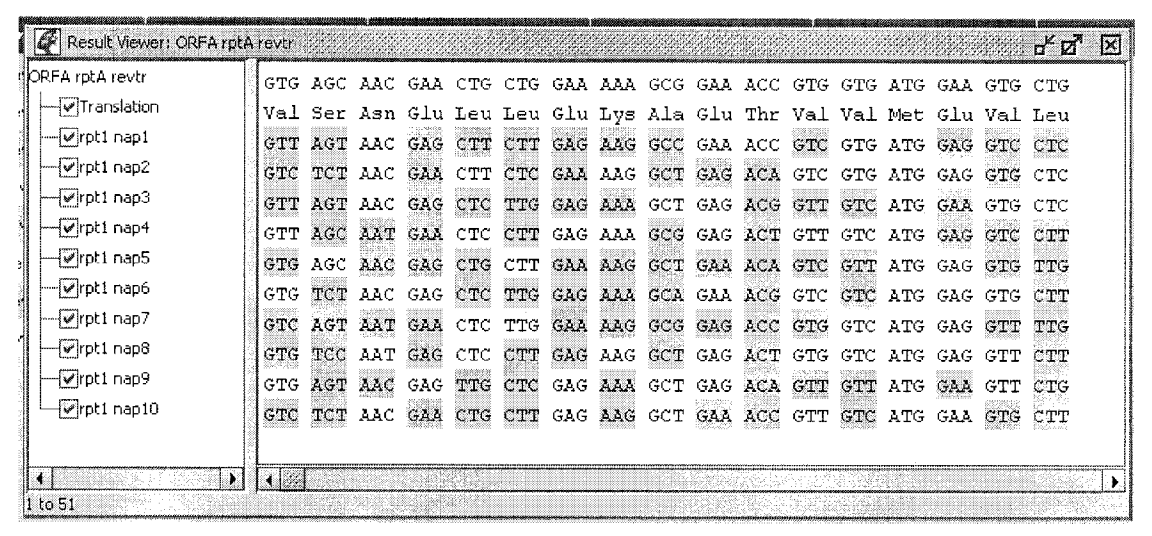

Step 4: The amino acid sequence translated from the individual DNA sequence was reverse-translated using the standard genetic code and a *B. napus* codon bias table. A biased codon table compiled from 530 *B. napus* protein coding regions was used, and each generated sequence was code-named "nap" (for "*napus*"), plus the version number. Thus, in the example of Repeat 1, the first reverse-translated, codon-biased sequence was named, "rpt1 nap1." In this particular illustration, this process was performed 10 times, to generate 10 DNA sequence versions encoding the protein sequence of Repeat 1, as shown in FIG. 5. More (or less) than 10 iterations could have been done. FIG. 5 illustrates the substantial sequence diversity generated in 10 iterations for the first 17 amino acids of Repeat 1.

Step 5: The 10 sequence versions of codon-optimized coding regions were exported into the corresponding number of text files.

Steps 3-5 were performed for each of the other repeated sequence domains. Thus, in this illustration, a total of 90 "nap" sequence versions were generated (10 for each repeated element). The 90 sequence files were then imported into the CLUSTALW™ program, Mega 3.1 (accessed at www-.megasoftware.net/), and a multiple sequence alignment was performed using all 90 sequences as input. Because these sequences are segments of protein coding regions, the alignments were performed with no gaps allowed.

Figure 6:
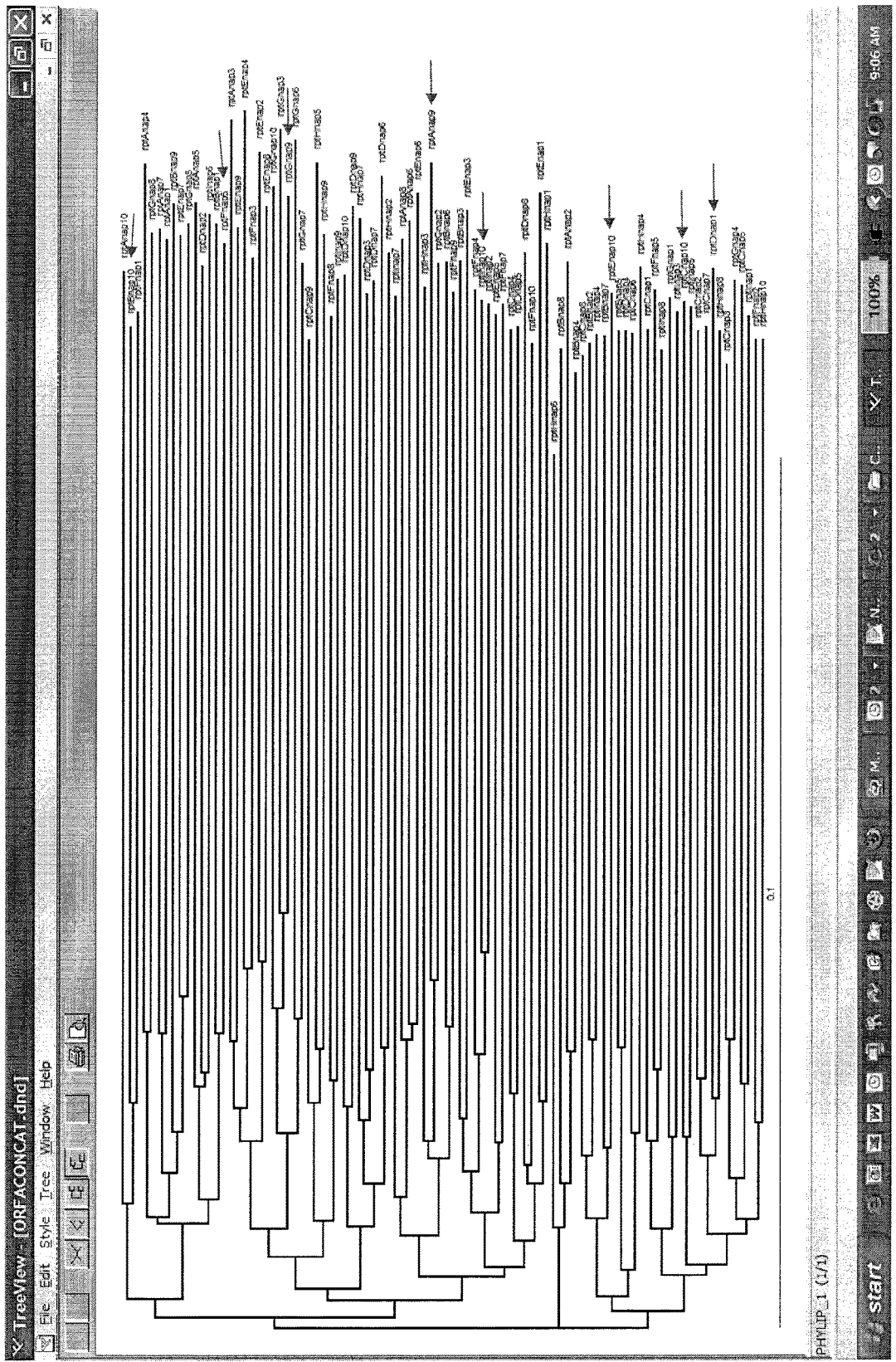
FIG. 6 includes a neighbor-joining tree output from the CLUSTALW™ program, Mega3.1, performing a sequence alignment of 90 *Brassica napus* codon-optimized sequences for *Schizochytrium* PUFA ORFA Repeats 1-9. Each repeat Repeat 1-9 is designated by a letter (e.g. rptA, rptB, rptC, rptD, rptE, rptF, rptG, rptH, rpt1), and each iteration of a *B. napus*-biased sequence is designated by a number, (e.g., nap1, nap2, nap3, nap4, nap5, nap6, nap7, nap8, nap9, nap10). Diverged sequences chosen in this example are marked by arrows, and for clarity a shorthand designation of the chosen diverged sequence is noted on the right side of the figure (e.g. rptBnap10 is designated as B10).

After CLUSTALW™ alignment, a neighbor-joining tree was assembled and visualized. One of the ten codon-optimized sequences for each of the nine repeated domains in the protein was selected. Each selected sequence version was chosen from a section of the tree that was deeply-branched. FIG. 6. From the 90 total sequences, only one sequence for each repeated element was selected.

The selected sequence for each repeated domain was incorporated into a codon-optimized DNA sequence encoding the entire protein, in the proper position for each particular repeat. Care was taken to maintain the correct reading frame. Final analyses of the entire codon-optimized sequence, including the separately designed diverged repeat elements, was performed to assure the absence of undesired motifs, restriction enzyme recognition sites, etc. Following final analyses of the entire codon-optimized sequence, care was taken when introducing changes in the sequence encoding the repeat elements to assure that codon and sequence diversity were maintained.

Figure 8:
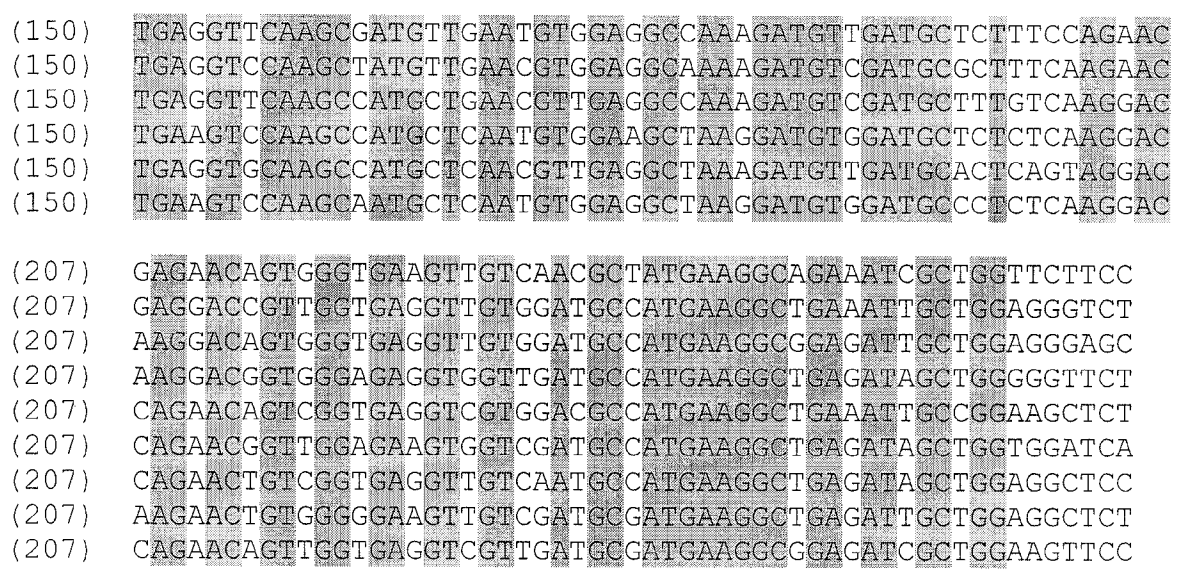

In this example, it is unlikely that the selected sequences are the most highly-diverged possible, because: 1) only 10 sequence iterations of each repeated domain were performed; and 2) the sequences were picked visually. However, it is certain that the sequences chosen are close to the optimal sequence (i.e., the most highly diverged possible), since they were chosen from the deepest branches of the neighbor-joining tree (i.e., they are the most distantly related to one another in this sequence set). Smith-Wasserman global alignments were done for all pair wise combinations, and the range of homology was 74-81%, with a probable median of 76-77%. FIG. 7. A CLUSTALW™ alignment of the chosen 9 newly-designed diverged coding regions for the 9 repeated domains (SEQ ID NOs:41-49) is shown in FIG. 8. Overall, they are 93.1% homologous and 61.7% identical (compared to 100% homologous and 89.7% identical for the native sequences).

Example 2

Expression of an Optimized Coding Sequence Containing Large Repeated DNA Sequences The DNA sequence for the entire optimized coding sequence as designed in Example 1 is synthesized by a commercial vendor according to standard industry practice.

The synthesized oligonucleotide molecule consisting of the entire optimized coding sequence is introduced into a *B. napus* cell to produce a *B. napus* cell comprising the optimized coding sequence, for example, by ligation of the oligonucleotide into an appropriate vector and subsequent *Agrobacterium*-mediated transformation.

The *B. napus* cell comprising the optimized coding region expresses the protein encoded by *Schizochytrium* PUFA synthase ORFA at levels higher than in a *B. napus* cell comprising the native coding sequence of *Schizochytrium* PUFA synthase ORFA.

Example 3

*B. napus* Plants Comprising an Optimized Coding Sequence Containing Large Repeated DNA Sequences The *B. napus* cell comprising the optimized coding sequence comprising diverged, codon-optimized amino acid repeat regions produced in Example 2 is utilized to regenerate a *B. napus* plant. The *B. napus* plant is then propagated to produce progeny that comprise the optimized coding sequence.

While the invention may be susceptible to various modifications and alternative forms, specific embodiments have been shown by way of example in the drawings and have been described in detail herein. However, it should be understood that the invention is not intended to be limited to the particular foul's disclosed. Rather, the invention is to cover all modifications, equivalents, and alternatives falling within the scope of the invention as defined by the following appended claims and their legal equivalents.

What may be claimed is:

1. A method for chemically synthesizing a nucleic acid molecule, the method comprising:
   (i) isolating an amino acid sequence that provides a polypeptide of interest, wherein the polypeptide of interest comprises at least one amino acid repeat region;
   (ii) extracting a nucleic acid sequence from the amino acid sequence and identifying at least one amino acid repeat region from the polypeptide of interest within the nucleic acid sequence;
   (iii) deducing a plurality of sample codon-optimized nucleic acid sequences that each encodes the amino acid sequence;
   (iv) aligning the plurality of sample codon-optimized nucleic acid sequences by sequence homology and assembling a neighbor-joining tree comprising the plurality of sample codon-optimized nucleic acid sequences;
   (v) selecting one of the plurality of sample codon-optimized nucleic acid sequences as a diverged, codon-optimized nucleic acid sequence, wherein the selected sample codon-optimized nucleic acid sequence is from the most deeply branched section of the neighbor-joining tree; and
   (vi) chemically synthesizing the nucleic acid sequence encoding the polypeptide of interest that includes the selected sample codon-optimized nucleic acid sequence.

2. The method according to claim 1, wherein preparing the amino acid sequence that provides the polypeptide of interest comprises obtaining a nucleic acid sequence that encodes the amino acid sequence from a genome database or cloning from a source genome.

3. The method according to claim 1, wherein deducing a plurality of sample codon-optimized nucleic acid sequences that each encodes the amino acid sequence comprises utilizing the codon-usage bias of an organism.

4. The method according to claim 1, wherein the polypeptide of interest is expressed in an organism.

5. The method according to claim 1, wherein the polypeptide of interest is a synthetic polypeptide that is not known to be expressed in an organism.

6. The method according to claim 1 wherein step (ii) through step (vi) are independently performed for at least some of the amino acid repeat regions in the polypeptide of interest.

7. The method according to claim 6, wherein step (ii) through step (vi) are independently performed for each of the amino acid repeat regions in the polypeptide of interest.

8. The method according to claim 1, wherein the chemically synthesized nucleic acid sequence in step (vi) comprises: (a) the nucleic acid sequence encoding the polypeptide of interest that includes the selected sample codon-optimized nucleic acid sequence, and (b) at least one regulatory element operably linked to the nucleic acid sequence.

9. The method according to claim 1, wherein the nucleic acid sequence is suitable for introduction into a host organism.

10. The method according to claim 8, wherein the nucleic acid sequence is suitable for introduction into a host organism.

11. The method according to claim 10, wherein the nucleic acid sequence is an expression vector.

* * * * *